United States Patent [19]

Kun et al.

[11] Patent Number: 5,583,155
[45] Date of Patent: Dec. 10, 1996

[54] 6-AMINO-1,2-BENZOPYRONES USEFUL FOR TREATMENT OF VIRAL DISEASES

[75] Inventors: Ernest Kun, Mill Valley, Calif.; Laure Aurelian, Baltimore, Md.

[73] Assignee: Octamer, Inc., Mill Valley, Calif.

[21] Appl. No.: 237,969

[22] Filed: May 3, 1994

Related U.S. Application Data

[63] Continuation of Ser. No. 845,342, Mar. 4, 1992, abandoned, which is a continuation of Ser. No. 585,231, Sep. 21, 1990, abandoned, which is a continuation-in-part of Ser. No. 412,783, Sep. 26, 1989, abandoned.

[51] Int. Cl.⁶ .................................................. A61K 31/35
[52] U.S. Cl. ..................................... 514/457; 514/456
[58] Field of Search ..................................... 514/456, 457

[56] References Cited

U.S. PATENT DOCUMENTS

| | | | |
|---|---|---|---|
| 4,248,789 | 2/1981 | Okada et al. | 549/399 |
| 4,382,951 | 5/1983 | Grasberger et al. | 514/456 |
| 4,460,578 | 7/1984 | Cervelle et al. | 424/195.1 |
| 4,904,690 | 2/1990 | Aono et al. | 514/456 |
| 4,906,656 | 3/1990 | Laks | 514/456 |

FOREIGN PATENT DOCUMENTS

| | | |
|---|---|---|
| 2062758 | 6/1971 | France . |
| 3-227923 | 1/1990 | Japan . |
| 2244646 | 11/1991 | United Kingdom . |
| WO89/07441 | 8/1989 | WIPO . |
| WO89/07939 | 9/1989 | WIPO . |
| WO89/09777 | 10/1989 | WIPO . |
| WO91/04663 | 4/1991 | WIPO . |

OTHER PUBLICATIONS

Chemical Abstracts 60: 15017(e) (1964).
Kokotos et al, "Syntheses and Study of Substituted Coumarins"; J. Heterocylcia Chem; vol. 23, pp. 87–92 (Jan.–Feb. 1986).
CA: 103: 33819x—Kokotos et al. (1985).
CA: 55: 5534d—Hoeksema et al (1961).
CA: 110: 231324q—Enomoto et al. (1989).
CA: 111: 232636a—Rao et al. (1989).
CA: 95: 169053s—Merchant et al. (1981).
CA: 88: 190637a—Khan et al. (1978).
CA: 102: 24528d—Merchant et al. (1985).
CA: 99: 105153z—Merchant et al. (1983).
Rice, W. et al., "Induction of endonuclease–mediated apoptosis in tumor cells by C–nitroso–substituted ligands of poly (ADP–ribose) polymerase". Proc. Natl. Acad. Sci. 89 7703–7707 (1992).
Buki, K. et al., "Destabilization of $Zn^{2+}$ coordination in ADP–ribose transferase (polymerizing) by C–nitroso–1, 2–benzopyrone coincidental with inactivation of the polymerase but not the DNA binding function". FEBS 290: 181–185 (1991).

Kirsten, E. et al., "Cellular Regulation of ADP–ribosylation of proteins IV. Conversion of poly (ADP–Ribose) polymerase activity to NAD–glycohydrolase during retinoic acid–induced differentiation of HL60 cells ". Experimental Cell Research 194:1–8 (1991).
Buki, K. et al., "Inhibitor binding of adenosine disphosphoribosyl transferase to the DNA primer site of reverse transcriptase templates". Biochem. Biophys. Res. Com. 180:496–503 (1991).
Cole, G. et al., "Inhibition of HIV–1 IIIb replication in AA–2 and MT–2 cells in culture by two ligands of poly (ADP–ribose) polymerase: 6–amino–1,2 benzopyrone and 5–iodo–6–amino–1,2–benzopyrone". Biochem. Biophys. Res. Com. 180:504–514 (1991).
Henderson, L. et al., "Primary structure of the low molecular weight nucleic acid–binding proteins of murine leukemia viruses" J. Biol. Chem. 256 (16) 8400–8403 (1981).
Gorelick, R. et al., "Point mutants of moloney murine leukemia virus that fail to package viral RNA: evidence for specific RNA recognition by a zinc –finger like protein sequence". Proc. Natl. Acad. Sci. 85:8420–8424 (1988).
Gorelick, R. et al., "Noninfectious human immunodeficiency virus Type 1 mutants deficient in genomic RNA". J. Virol. 64:3207–3211 (1990).
Meric, C. et al., "Characterization of moloney murine leukemia virus mutants with single amino acid substitutions in the Cys–His box of the nucleocapsid protein". J. Virol. 63:1558–1568 (1989).
Aldovini, A. et al., "Mutations of RNA and protein sequences involved in human immunodeficiency virus Type I packaging result in production of noninfectious virus". J. Virol. 64:1920–1926 (1990).
Lever, A. et al., "Identification of a sequence required for efficient packaging of human immunodeficiency virus Type I RNA into virions". J. Virol. 63:4085–4087 (1989).
Gradwohl, G. et al., "The second zinc–finger domain of poly (ADP–ribose) polymerase determines specificity for single-stranded breaks in DNA". Proc. Natl. Acad. Sci. 87 2990–2994 (1994).
South, T. et al., "113 Cd NMR studies of 1:1 Cd adduct with an 18–residue finger peptide from HIV–1 nucleic acid binding protein, p7". J. Am. Chem. Soc. 111 395–396 (1989).
South, T. et al., "Zinc fingers and molecular recognition. Structure and nucleic acid binding studies of an HIV zinc fingerlike domain". Biochem. Pharm. 40:123–129 (1990).

(List continued on next page.)

*Primary Examiner*—T. J. Criares
*Attorney, Agent, or Firm*—Albert P. Halluin; Scott R. Bortner; Pennie & Edmonds

[57] ABSTRACT

Unsubstituted or substituted 6-amino-1,2-benzopyrones are potent, selective and non-toxic inhibitors and suppressants of viral infections in a mammalian host. The compounds are particularly useful for treatment of AIDS, herpetic episodes and cytomegaloviral infections. The method of treatment of viral diseases by 6-amino-1,2-benzopyrones is described.

9 Claims, 14 Drawing Sheets

OTHER PUBLICATIONS

Summers, M. et al., "High–resolution structure of an HIV zinc fingerlike domain via a new NMR–based distance geometry approach". Biochemistry 29:329–340 (1990).

Yamagoe, S. et al., "Poly (ADP–ribose) polymerase inhibitors suppress UV–induced human immunodeficiency virus type 1 gene expression at the posttranscriptional level". Molecular and Cellular Biology 11(7) 3522–3527 (199 1).

Krasil'Nikov, I. et al., "Inhibitors of ADP–ribosylation as antiviral drugs: Experimental study of the model of HIV infection". VOPR. VIRUSOL (Russia) 36(3) 216–218 (1991).

Furlini, G. et al., "Increased poly (ADP–ribose) polymerase activity in cells infected by human immunodeficiency virus type–1". Microbiologica 14(2) 141–148 (1991).

Ibne–Rasa, K. et al., "O–Nitrosobenzamide. A possible intermediate in the von Richter reaction". J. Org. Chem. 47(24) 4664–4670 (1982).

Seidel, W. et al., "Oxidation of aromatic hydrazides". Chemical Abstracts 82 82 Col. 16505X (1975).

Wubbels, G. et al., "Mechanism of water–catalyzed photo–isomerization of p–nitrobenzaldchyde". J. Org. Chem. 47(24) 4664–4670 (1982).

Kovacic, P. et al., "Reduction potentials in relation to physiological activities of benzenoid and heterocylic nitroso compounds: comparison with the nitro precursors". Bioorganic Chemistry 18: 265–275 (1990).

Ehlhardt, W. J. et al., "Nitrosoimidazoles: highly bactericidal analogues of 5–nitroimidazole drugs". J. Med. Chem. 31: 323–329 (1988).

McClelland, R. A. et al., "Products of the reductions of 2–nitroimidizoles". J. Am. Chem. Soc. 109: 4308–4314 (1987).

Noss, M. B. et al., "Preparation, toxicity and mutagenicity of 1–methyl–2–nitrosoimidazole". Biochem. Pharm. 37: 2585–2593 (1988).

Varghese, A. J. et al., "Modification of guanine derivatives by reduced 2–nitrosoimidazoles". Cancer Research 43: 78–82 (1983).

Buki, K. et al., "Destabilization of Zn(II) coordination in poly(ADP–Ribose) polymerase by 6–nitroso–1,2–benzopyrone coincidental with inactivation of the polymerase but not with the DNA binding function". The Paul Mandel International Meeting of Poly (ADP–Ribosyl)ation Reactions. Abstract 22C May 30, 1991.

Mulcahy, R. T. et al., "Cytotoxicity and glutathione depletioni by I–methyl–2–nitrosoimidazole in human colon cancer cells". Biochem. Pharm. 38: 1667–1671 (1989).

Noss, M. B. et al., "I–Methyl–2–nitrosoimidazole: cytotoxic and glutathione depleting capabilities". Int. J. Radiation Oncology Biol. Phys. 16: 1015–1019 (1989).

D. Locke, *Virus Diseases—A. Layman's Handbook*, pp. 1–6 (1978), Crown Publ. New York.

*The Merck Manual*, p. 170 (1982).

A. Hakam et al., "Catalytic Activities of Synthetic Octadeoxyribonucleotides as Coenzymes of Poly(ADP–Ribose) Polymers and the Identification of a New Enzyme Inhibitory Site", FEBS Letters 212 (1), :73–78 (1987).

C. Dery et al., "Possible Role of ADP–Ribosylation of Adenovirus Core Proteins in Virus Infection", Virus Research 4:313–329 (1986).

S. J. Child, "Inhibition of Vaccinia Virus Replication by Nicotinamide: Evidence for ADP–Ribosylation of Viral Proteins", Virus Research 9:119–132 (1988).

G. A. Cole et al., "Inhibition of HIV–1 IIIb Replication in AA–2 and MT–2 Cells in Culture by Two Ligands of Poly (ADP–Ribose) Polymerase ", B.B.R.C. 180(2): 504–514 (1991).

H. Kitagawa et al., "Coumarian Derivatives for Medicinal Purposes", Chem. Abstr., 52 Abstract No. 18874 (1958).

R. Rajeshwar, "Mercaptocoumarinoxazoles", Chem. Abstr. 111, Abstract No. 232636 (1989).

J. R. Merchant, "Synthesis of Some Benzopyranocyclopentapyridine and Pyranoacridine Derivatives", Chem. Abstr. 99, p. 577, Abstract No. 105153 (1989).

B. Sreenivasulu et al., "Search for Physiologically Active Compounds", Chem. Abstr. 82, p. 498, Abstract No. 111917 (1975).

6-AMINO-1,2-BENZOPYRONES USEFUL FOR TREATMENT OF VIRAL DISEASES

The present invention was made in the course of research supported by the U.S. Department of Defense, Air Force Office of Scientific Research Grants AFOSF-86-0064 and AFOSR-89-0231. The U.S. Government may have certain rights in this invention.

This is a continuation of application Ser. No. 07/845,342, filed Mar. 4, 1992, now abandoned, which is a continuation of application of Ser. No. 07/585,231 filed on Sep. 21, 1990, now abandoned which is a continuation-in-part of the application Ser. No. 07/412,783 filed on Sep. 26, 1989, now abandoned.

BACKGROUND OF THE INVENTION

1. Field of the Invention

The present invention relates generally to a method of treatment of viral diseases using 6-amino-1,2-benzopyrones as antiviral agents. More specifically, it relates to the use of 6-amino-1,2-benzopyrones, their homologues and salts, in suppressing and inhibiting the growth of viruses in a mammalian host. These compounds are particularly effective inhibitors of human immunodeficiency virus, herpes simplex virus and cytomegalovirus and are therefore particularly useful for treatment of AIDS, herpetic episodes and cytomegaloviral infections. Moreover, these compounds have very low, if any, toxicity.

2. The State of Art and Related Disclosures

Viral infections became one of the most serious problem of the modern society. Their high degree of infectiousness and a fast reproduction cycle within the host organism, combined with essentially no effective treatment available aside of largely toxic desoxyribonuclotide homologs, make the viruses a nuisance and health hazard which the human population encounters on daily basis.

Viruses are intracellular parasitic molecular particles consisting essentially of a central core nucleic acid surrounded by an outer cover of protein. For their reproduction, viruses are wholly dependent on the host cells.

Several hundred different viruses are know to cause infection in man. Because of their wide prevalence, the viral diseases create important medical and public health problems. Included among them is the most common of all viral diseases, the influenza which alone is responsible for one billion episodes of disease every year in the United States alone, or such highly infectious viral diseases as measles, chickenpox, rabies, herpetic viral diseases, cytomegaloviruses and human immunodeficiency virus causing AIDS. All these viruses are spread quickly by man himself, mainly via respiratory and enteric excretions or by contact. Moreover, some of the viruses are very resistant to any treatment and some of them, for example herpes simplex viruses or cytomegalovirus, once inside the body, may remain forever in a dormant state until the resistance is weakened. The others, such as human immunodeficiency virus is nearly always fatal.

There is no simple treatment of viral diseases. They are not susceptible to antibiotics and there is no other available treatment of viral diseases other than by chemotherapy which inhibits viral replication in the host cells. *The Merck Manual*, 170 (1982). Examples of these chemical agents are idoxuridine (IDU) useful for treatment of herpes simplex keratitis and methisazone active against influenza A virus. The other known viral replication inhibitors are acyclovir, ribavirin, vidarabine, gancyclovir, adenine arabinoside (ARA-A) and AZT. These, and other viral replication inhibitors, however, are known to be cytotoxic, hepatotoxic, neurotoxic, nephrotoxic and were shown to have teratogenic effects. *Virus Diseases*, 1–6 (1978), Crown Publishers, N.Y.

Thus it would be highly desirable to have available an effective and yet nontoxic treatment of viral diseases.

Human immunodeficiency virus (HIV) infections presently constitute one, if not the most pressing health hazard worldwide. Known as acquired immunodeficiency syndrome (AIDS), HIV infections are almost always fatal because due to a weakened immunoresistance, they are quickly accompanied by opportunistic infections, malignancies and neurologic lesions leading to an early death.

HIV term encompasses a group of retroviruses known and termed human T-lymphotropic virus Type III, (HTLV-III), lymphadenopathy-associated virus (LAV) and retrovirus (ARV).

Retroviruses contain an enzyme called reverse transcriptase that can convert viral RNA in the cytoplasm into DNA, which may replicate from extrachromosomal sites or move into the cell nucleus where it becomes part of the host cell DNA. These integrated viral genes are duplicated with normal cellular genes, and all progeny of the originally infected cells will contain the viral genes. Expression of the viral genes for some retroviruses may be oncogenic, converting the cell into a cancer, or may have other pathologic effects which may alter normal cell function or produce cell death.

AIDS patients experience a broad spectrum of acute or chronic clinical problems such as lymphadenopathy, weight loss, intermittent fever, malaise, lethargy, chronic diarrhea, lymphopenia or, anemia, with full blown AIDS syndrome consisting of any of the above symptoms combined with the whole scale of opportunistic infections, such as pneumocystis carinii pneumonia, candidiasis, mycobacterial infections, cytomegalovirus or herpes simplex virus infections, to name a few, or with secondary cancers, such as Kaposi's sarcoma and various lymphomas. These opportunistic and secondary infections cause more than 90% fatality in AIDS patients.

There is no effective treatment for AIDS other than that of the opportunistic infections, neoplasms and other complications. Available cytostatic (AZT) and antiviral (acyclovir) drugs are mostly extremely toxic and consequently cause severe side effects. Because of its fatality and because of the lack of treatment for AIDS patients, enormous efforts are aimed at development of effective anti-HIV drugs or vaccines. The most promising of all those currently investigated seem to be antiviral drugs which may somehow inhibit the viral reproduction enzyme, reverse transcriptase. *The Merck Manual*, 15th Ed., 288 (1987).

To provide an effective and yet non-toxic antiviral drug which would effect the reproduction of HIV would thus be of extreme importance and life saving measure for many thousands of AIDS victims.

Herpes simplex virus type-1 and 2 similarly are wide spread infections. They may occur in AIDS patients as one of the opportunistic infections. HSV-2 has been related to the development of uterine cancer.

Herpes simplex, also called fever blister and cold sore is one of the most prevalent viral infection. The infecting agent is the relatively large herpes simplex virus herpesvirus hominis (HVH). There are two HVH strains. Type-1 strain (HSV-1) commonly causes herpes labialis located on a lip, and keratitis, an inflammation of the cornea. Type-2 is usually located on or around genital area and is generally transmitted primarily by direct contact with herpetic sore or lesions.

Estimated frequency and location of oral (HSV-1) and genital (HSV-2) infections are about half million of primary cases of type-1 per year, with 98 million of recurrent cases per year in the United States alone. Of the genital HSV-2 cases, there are around 500,000 cases of primary genital herpes with 3–9 million of recurrent cases per year in the United States. *Living With Herpes,* 1–11, (1983), Doubleday and Company, N.Y.

Herpes simplex virus is very infectious and is rapidly and easily transferable by contact. There is no specific therapy to this extremely painful viral infection. Corticosteroids, if given early, may relieve pain in severe cases. Aspirin and other anti-inflammatories or antiviral agents systemically may alleviate the pain. However, these agents have the same undesirable side effects as those discussed previously. Treatment of HSV infections is primarily by systemic administration of antiviral drugs, such as for example with highly cytotoxic IDU and trifluridine (TFT), with ARA-A, and with acyclovir or bromovinyldeoxyuridine semi-specific enzyme inhibitors of virus replication.

Since the primary route of administration of these agents is systemic, severe side effects were shown to accompany such treatments. Moreover, these agents are not selective inhibitors of the herpes simplex virus replication but effect also a replication of normal cells. Therefore, when used in doses large enough to seek and destroy all the active herpes viruses dormant in the sensory ganglia, these compounds may also be highly disruptive to the normal DNA in the host cells in which the virus multiplies. This is a very undesirable effect since the replication of normal cells is also effected.

Thus, it would be advantageous to have available non-toxic treatment of HSV infections.

Cytomegalovirus (CMV) is often a dangerous co-infection of HIV. The human CMVs are a subgroup of highly infectious agents having the propensity for remaining latent in man. CMVs are very common among the adult population and as many as 90% of adults have been exposed to and experienced CMVs infections. CMVs are normally present in body liquids such as blood, lymph, saliva, urine, feces, milk, etc. Congenital CMV infections may cause abortion, stillbirth, postnatal death from hemorrhage, anemia or severe hepatic or CNS damage. In adults, CMV infection may be asymptomatic but may also cause hepatitis, atypical lymphocytosis or blindness. Particularly dangerous are CMS infections afflicting AIDS patients, where CMV may cause pulmonary, gastrointestinal or renal complications.

There is no specific therapy for CMVs. Contrary to the HSV, CMV is resistant to acyclovir, a potent and very toxic anti-viral drug and to other known antiviral drugs.

Thus, it would be extremely advantageous to have available the drug which would effectively inhibit CMV infections.

The existing chemotherapeutical treatment of the most viral infections is thus mostly limited to very toxic agents and antivirals.

It is therefore a primary object of this invention to provide a non-toxic, highly effective antiviral drugs. 6-amino-1,2-benzopyrones (6-ABP) seem to be a group of such prototype antiviral drug.

This drug, (6-ABP) has been now found to be an agent of remarkably low toxicity, yet highly effective viral inhibitor in cell cultures and in human blood. Its antiviral spectrum appears to be particularly useful for treatment of the most dangerous viral infections, such as above described infections caused by HIVs, CMVs and HSVs. However it may be equally effective in treatment of other viral diseases.

6-aminobenzopyrone has been known and described in *J. Pharm. Soc. Jap.*, 498:615–628 (1923). However, only scarce medicinal use of this substance has been reported, although the testing was done for sedative and hypnotic effects (*J. Pharm. Soc. Japan,* 73:351 (1953) and Ibid, 74:271 (1954). Hypothermal action was studied but it was found that 6-amino group decreased the hypothermal effect *Yakugaku Zasshi,* 78:491 (1958). Some antipyretic, hypnotic, hypotensive and adrenolytic action was reported, Ibid, 83:1124 (1963).

Related molecule, 1,2-benzopyrone (coumarin) was shown to be an inhibitory ligand of adenosinediphosphoribose transferase (ADPRT), a DNA-binding nuclear protein present in neoplastic cells (*Proc. Nat. Acad. Sci. (USA),* 84:1107 (1987)).

Further research showed that 6-ABP is specifically binding to ADPRT at the same site that also binds catalytically effective DNA termini. Thus, both 6-ADP and DNA compete for the same site on ADPRT. These results were disclosed in *FEBS Lett.,* 212:73 (1987), where the biological role of ADPRT was studied extensively with the aid of synthetic ligands of ADPRT and shown to inhibit DNA proliferation, particularly in tumorigenic cells.

The primary object of this invention is the discovery that 6-ABPs, previously known to have only limited biological utility, are specific, selective, potent and non-toxic antiviral agents. The testing of these compounds on various virally infected cultures, including HIV infected human lymphoblasts, showed that 6-ABP are particularly useful for inhibition of HIV, HSV and CMV replication.

SUMMARY

One aspect of the current invention concerns a method for treatment of viral infections in a mammal comprising administering to a mammal a therapeutically effective amount of a compound of the formula

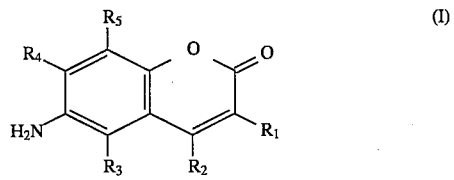

wherein $R_1$, $R_2$, $R_3$, $R_4$, or $R_5$ are each independently selected from hydrogen, hydroxy, amino, alkyl, alkoxy, cycloalkyl or phenol, optionally substituted with alkyl, alkoxy, hydroxy or halo, or a pharmaceutically acceptable salt thereof.

Other aspect of the current invention concerns a method for inhibiting or suppressing viral reproduction in a mammal comprising administering to the mammal a therapeutically effective amount of a compound of the formula

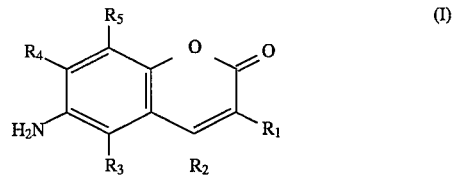

wherein $R_1$, $R_2$, $R_3$, $R_4$, or $R_5$ are each independently selected from hydrogen, hydroxy, amino, alkyl, alkoxy, cycloalkyl or phenol, optionally substituted with alkyl, alkoxy, hydroxy or halo, or a pharmaceutically acceptable salt thereof.

Another aspect of the current invention relates to an antiviral agent having the formula

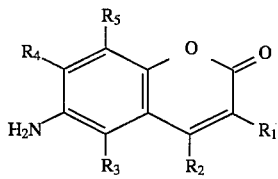

wherein $R_1$, $R_2$, $R_3$, $R_4$, or $R_5$ are each independently selected from hydrogen, hydroxy, amino, alkyl, alkoxy, cycloalkyl or phenol optionally substituted with alkyl, alkoxy, hydroxy or halo, provided that $R_1$, $R_2$, $R_3$, $R_4$ and $R_5$ cannot be hydrogen or that $R_1$ cannot be unsubstituted phenyl at the same time, or a pharmaceutically acceptable salt thereof.

Still another aspect of this invention is the method of treatment of viral diseases caused by HIVs, HSVs or CMVs by administering to a mammal therapeutically effective amount of compound of formula

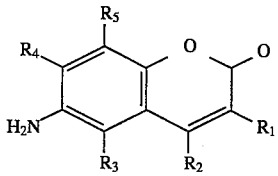

wherein $R_1$, $R_2$, $R_3$, $R_4$, or $R_5$ are each independently selected from hydrogen, hydroxy, amino, alkyl, alkoxy, cycloalkyl or phenol optionally substituted with alkyl, alkoxy, hydroxy or halo, or pharmaceutically acceptable salt thereof.

BRIEF DESCRIPTION OF DRAWINGS

FIG. 1 shows the inhibitory effect of 6-ABP on HSV growth in pretreated cell culture, wherein

DETAILED DESCRIPTION OF THE INVENTION

Definitions

Figure 1A:
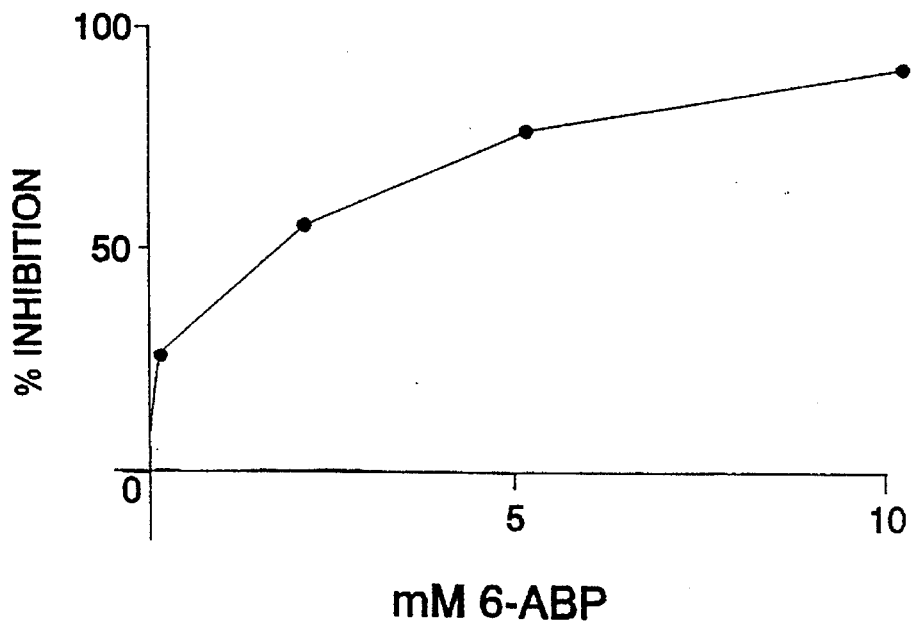
FIG. 1A shows % inhibition of viral growth of HSV-1 strain F, as a function of the external drug concentration

As used herein:

"6-ABP" refers to 6-amino-1,2-benzopyrone of formula (I) substituted or unsubstituted on $R_1$, $R_2$, $R_3$, $R_4$ or $R_5$ corresponding to coumarin carbons 3, 4, 5, 7 and 8, respectively, with hydrogen, hydroxy, amino, alkyl, alkoxy, cycloalkyl, or phenyl optionally substituted with alkyl, alkoxy, hydroxy or halo.

"Pharmaceutically acceptable acid addition salt" refers to those salts which retain the biological effectiveness and properties of the free bases inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"ADPRT" refers to adenosinediphosphoribose transferase also known as poly (ADP-ribose)polymerase, (EC 2.4.99), a specific DNA-binding nuclear protein of eucaryotes that catalyzes the polymerization of ADP-ribose. The enzymatic process is dependent on DNA. ADPRT enzyme is modified by 6-amino-1,2-benzopyrone in the manner described below.

"Alkyl" refers to saturated or unsaturated branched or straight chain hydrocarbon radical. Typical alkyl group includes methyl, ethyl, propyl, isopropyl, butyl, isobutyl, tertiary butyl, pentyl, hexyl and the like.

"Alkoxy" refers to the radical -0-alkyl. Typical alcoxy radicals are methoxy, ethoxy, propoxy, butoxy and pentoxy and the like.

"Cycloalkyl" refers to a saturated monocyclic hydrocarbon radical containing 3–8 carbon atoms such as cyclopropyl, cyclobutyl, cyclopentyl, cyclohexyl, cycloheptyl and cyclooctyl.

"Substituted phenyl" refers to all possible isomeric phenyl radicals mono or disubstituted with a substituent selected from the group consisting of alkyl, alkoxy, hydroxy or halo.

Preparation of 6-Aminobenzopyrones

Aminobenzopyrones of this invention are compounds having a general formula

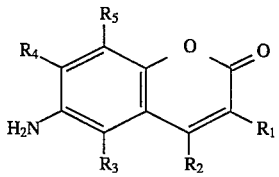

wherein the $R_1$, $R_2$, $R_3$, $R_4$ and $R_5$ are independently chosen from hydrogen, hydroxy, amino, alkyl, alkoxy, cycloalkyl or phenyl which may be optionally substituted with alkyl, alkoxy, hydroxy, or halo.

Of this group of compounds, only two compounds namely 6-amino-1,2-benzopyrone and 6-amino-3-phenyl-1,2-benzopyrone were previously described in *J. Pharm. Soc. Jap.*, 498:615 (1923) and in *Kogyo Kagaku Zaschi*, 71:1010 (1968) respectivitely. Some medical or pharmacological use of this compound were described in the art cited above.

Antitumorigenic activity was disclosed in U.S. patent application "6-Amino-1,2-Benzopyrone Antitumorigenic Agents and Method", Ser. No. 07/154,853 filed Feb. 10, 1988, which is hereby incorporated by reference. However, no antiviral activity was ever disclosed until this invention.

The synthesis of 6-ABP by the spontaneous reduction of 6-nitrocoumarin, obtained from Aldrich, by iron powder in acetic acid followed by filtration, rotary evaporation of acetic acid, extraction into ether and crystallization from ethanol is described in *FEBS Letters*, 212:73 (1987) and the better mode of synthesis is described in Example 1.

General reaction for preparation of 6-ABP, wherein $R_1$, $R_2$, $R_3$, $R_4$ and $R_5$ are hydrogen, hydroxy, amino, alkyl, alkoxy, cycloalkyl or phenyl is shown in Reaction Scheme 1.

Reaction Scheme 1

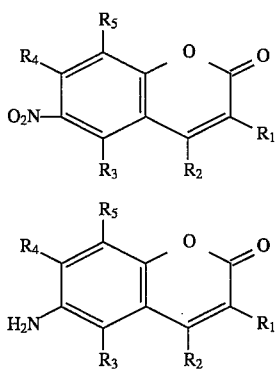

Many of the substituted compounds may be prepared in the same or similar way, using appropriately substituted 6-nitrocompound (A), commercially available.

Other compounds for which no substituted precursors are available must be synthesized by other reactions as described below.

Alkyl derivatives of 6-ABP are typically prepared from alkylated 1,2-benzopyrones commercially available or prepared as described in available chemical literature. Typically, for example 7-methyl-1,2-benzopyrone, commercially available from Aldrich and synthetic 3-methyl-1,2-benzopyrone prepared according *Synthesis*, 599 (1975) and 4-methyl-1,1,2-benzopyrone Ibid, 464 (1977) are nitrated using nitric acid in glacial acetic acid (*Indian J. Chem.*, 7:49 (1969)), giving predominantly the 6-nitro-derivatives as described in *Egypt. J. Chem.*, 20:453 (1977), which are reduced to the 6-amino-derivatives using sodium borohydride with Pd(C) catalyst in aqueous methanol using method described in *J. Heterocylic Chem.*, 23:87 (1986). Other alkylated compounds are prepared in the same way.

Cycloalkyl derivatives of 6-ABP are prepared by way of an example using the cyclohexyl group to substitute the methyl group in the synthesis of 4-methyl-1-1,2-benzopyrone *Synthesis*, 474 (1977). The resulting 4-cyclohexyl-1,2-benzopyrone is nitrated in the 6-position using acid, preferably nitric acid in glacial acetic acid, and then is reduced to the corresponding 6-amino compound by means of sodium borohydride with Pd(C) catalyst in aqueous methanol. Other cycloalkyls are prepared in the same way.

Aryl derivatives of 6-ABP are prepared by using method described in *Kogyo Kagaku Zasshi*, 71:110 (1968) and in *Chem. Abstr.*, 70:30023 (1969). As an example, the p-tolyl group is substituted for the phenyl group in the synthesis of 6-amino-3-phenyl-1,2-benzopyrone to give 6-amino-3-p-tolyl-1-2 benzopyrone. Other aryl derivatives are prepared in the same or similar fashion.

Hydroxy derivatives of 6-ABP are typically prepared from commercially available synthetic precursors such as 4-hydroxy- and 7-hydroxy-1,2-benzopyrone (Aldrich) by nitrating these precursors using nitric acid in glacial acetic acid according to *Indian J. Chem.*, 7:49 (1969) giving the corresponding 6-nitro-derivatives which are then reduced to 4-hydroxy- and 7-hydroxy-6-amino-1,2-benzopyrone by means of sodium borohydride with Pd(C) catalyst in aqueous methanol. Other hydroxylated 6-ABP are prepared in the same fashion.

Alkoxy derivatives are typically easily prepared from above described hydroxy derivatives. Typically, the 6-nitro-derivatives of the 4-hydroxy- and 7-hydroxy-1,2-benzopyrones mentioned above, are treated with dimethyl sulfate according to *Synthesis*, 144 (1978) to convert their hydroxy groups to methoxy groups, and then the resulting compounds are reduced to 4-methoxy- and 7-methoxy-6-amino-1,2-benzopyrone using sodium borohydride with Pd(C) catalyst in aqueous methanol. Other alkoxy compounds are prepared in the same or similar fashion.

Amino derivatives of 6-ABP are prepared, for example by using precursors having the additional amino group(s) substituents on $R_1$–$R_5$, such as for example, synthetic 3-amino-6-nitro-1,2-benzopyrone prepared according to *Arch. Pharm.*, 296:365 (1963) which is then reduced to 3,6-diamino-1,2-benzopyrone using sodium borohydride with Pd(C) catalyst in aqueous methanol. The other di- or triaminoderivatives are prepared in the same way.

The most preferred compound of the current invention is 6-amino-1,2-benzopyrone (6-ABP). However, the amino substitution in 6-position in combination with hydrophilic and hydrophobic substitution $R_1$, $R_2$, $R_3$, $R_4$ and $R_5$ in 1,2-benzopyrone (coumarin) positions 3, 4, 5, 7 and 8, confers similar or better biological activity on these variants of 6-ABP, and are intended to be within the scope of this invention.

Antiviral Activity

6-ABP compounds have been found to be potent and nontoxic pro-drugs which very specifically and effectively inhibit the viral DNA replication. Findings summarized in Examples 2–8 suggest the existence of a highly specific mechanism, by which 6-ABP inhibits viral DNA replication. 6-ABP is a "pro-drug" which penetrates most mammalian cells to a limited degree at physiological pH 7.2–7.4. In the cell, 6-ABP undergoes rapid oxidation at the 6-amino position to 6-nitroso-1,2 benzopyrone (6-NBP) which is the reactive species.

In the cell, the drug 6-ABP is quickly oxidized into 6-nitroso-1,2-benzopyrone. 6-NBP binds specifically and with high affinity to zinc-fingers of enzyme ADPRT and by oxidizing the SH group of zinc fingers to —S—S— group thus eliminates or ejects zinc from ADPRT. Zinc ejection metabolically inactivates ADPRT and converts it to a selective DNA binding protein. This protein then binds to the DNA structure and inhibits DNA replication. ADPRT, which possesses a 6-ABP site exclusively, thus becomes a very selective inhibitor of viral and tumorigenic replication.

The high reactivity of 6-ABP oxidation product 6-NBP is caused by its swift reaction with cellular glutathione reducing it back to 6-ABP. This explains the absence of non specific cellular toxicity of this drug, and the presence of its high efficacy by virtue of its specific binding to its own ADPRT site. Since the 6-ABP binding site is exclusive for ADPRT, no other enzymes are activated or inhibited by 6-ABP and, consequently, the 6-ABP drug is completely non-toxic. The toxicity studies are described in Example 8.

The apparent low toxicity of 6-ABP can be further explained by the rapid metabolic reduction of the intracellularly generated 6-NPB derivative by reduction of glutathione to the hydroxylamine and eventually to 6-ABP. This futile reduction-oxidation cycle is high in liver but much lower in target cells, such as for example lymphatic cells.

6-ABP has been found to be a specific, potent and nontoxic inhibitor of HIVHSV and CMV. However, 6-ABP is not a specific retro-viral inhibitor, since it is effective also in HSV and in other nonretroviral viruses. Its antiviral specificity is related to the inhibition of specific binding sites and integration steps and to Zn-fingers containing proteins in certain viruses. Consequently, the growth of any virus the DNA of which involves ADPRT would be inhibited with 6-ABP.

An antiviral activity of 6-ABP compounds was tested on cell cultures infected independently with human immunodeficiency virus, herpes simplex virus and cytomegalovirus and on some cell cultures transfected with two viruses. The actual experimental procedures are described in Examples 2–8 and the results are shown in FIGS. 1–12.

The inhibitory effect of 6-ABP compounds on HSV grown on HEp-2 cell cultures was determined by virus titration using plaque assay under liquid overlay conditions. The result of the following experiments studying the effects of varying concentration of the drug and conditions of drug exposure are summarized in FIGS. 1–5.

Figure 1B:
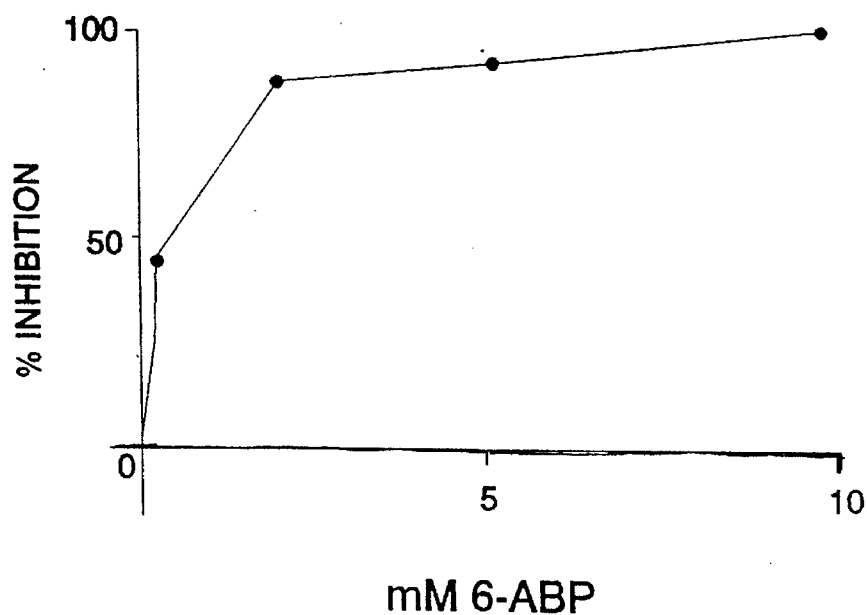
FIG. 1B shows % of the same inhibitory effect for HSV-2 strain G.

FIG. 1A illustrates the effect of drug 6-ABP exposure to cells. The cell were preexposed for 24 hrs to the drug to ensure adequate time for equilibration of the drug inside the cell with external drug concentration. The curve in FIG. 1A illustrates the percent inhibition of HSV-1 grown as a function of the external drug concentration. As seen from the curve, 6-ABP at 2 mM concentration was able to inhibit more than 50% of the growth of HSV-1 strain F, while 5 mM concentration inhibits around 80% of HSV-2 strain G. (FIG. 1B)

As seen from the curves 1A and 1B, in HEp-2 cell pretreated for 24 hours with the drug, the 50% inhibition of growth was achieved at concentration of 2 mM 6-ABP in HSV-1 strain F. The sensitivity of the HSV-2 strain G, to 6-ABP treatment is even better with about 45% inhibition achieved with 0.2 mM of 6-ABP and around 90% inhibition achieved with 1 mM of the drug and between 90–97% of inhibition of HSV-2 strain G, growth achieved with doses between 1–10 mM.

The above results show the high potency of 6-ABP drug on HSV viruses, which potency changes with the type of virus (HSV-1 v. HSV-2).

Figure 2A:
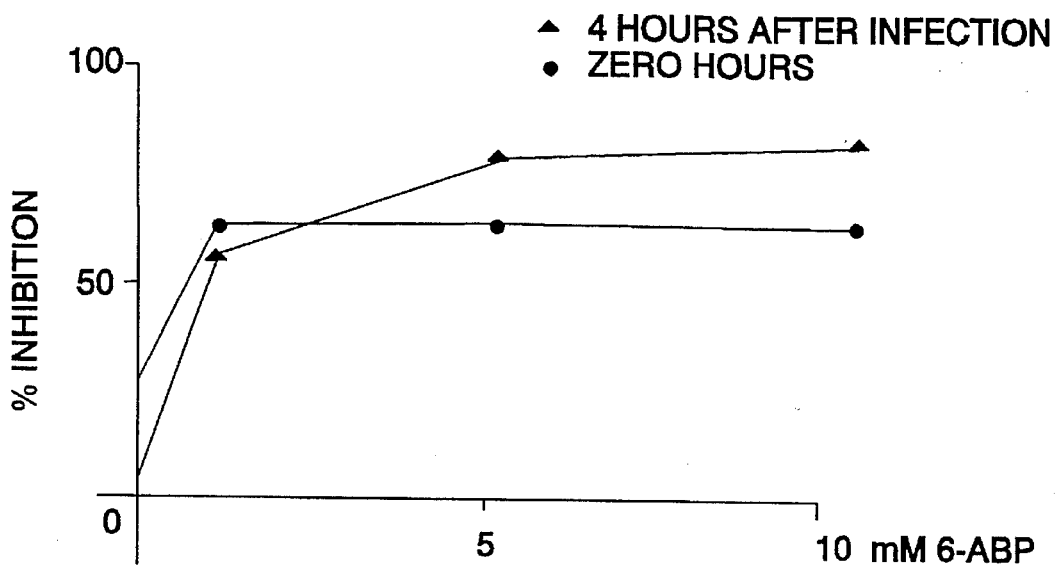
FIG. 2 compares the effect of 6-ABP treatment at the time of infection and four hours after the infection on HSV-1 strain F (FIG. 2A) and HSV-2 G (FIG. 2B) when the drug is added together with virus at zero time or four hours after viral exposure.
Figure 2B:
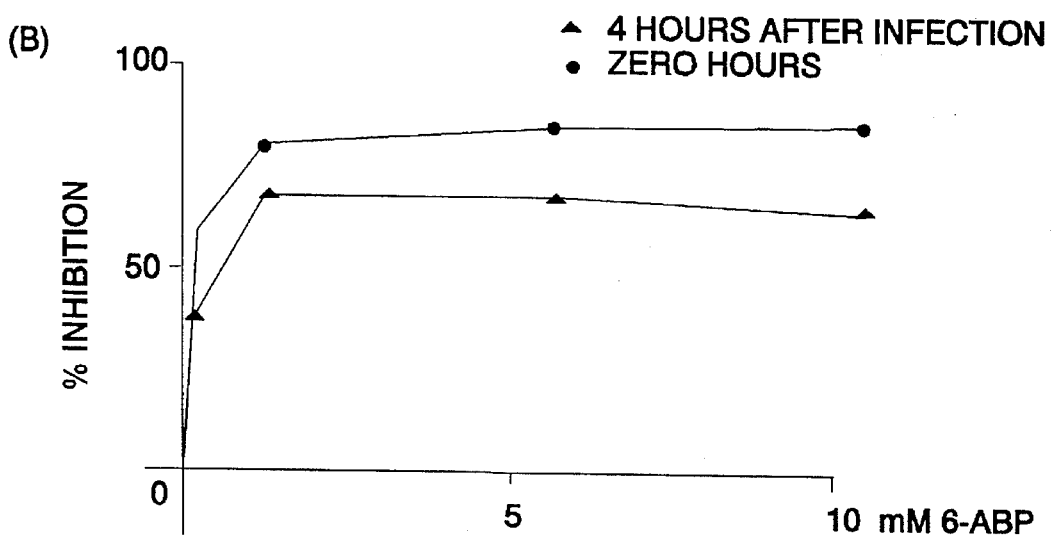

In the experiments illustrated in FIGS. 2A and 2B, a comparison was made between the time when the drug was added to the cell culture infected with HSV-1 (F) and HSV-2 (G) and time of infection. The drug 6-ABP in amount of 1, 5 and 10 mM was added to the cell culture at the time of viral infection (time zero) and 4 hours after the infection, when the early virus function leading to virus replication has already been expressed. As seen from FIGS. 2A and 2B, there were essentially no differences found between the two modes of drug exposure with the somehow higher effectivity of drug at the zero time exposure. The apparent greater effectivity of the drug for HSV-2 (G) is in agreement with results shown in FIGS. 1A and 1B.

Figure 3:
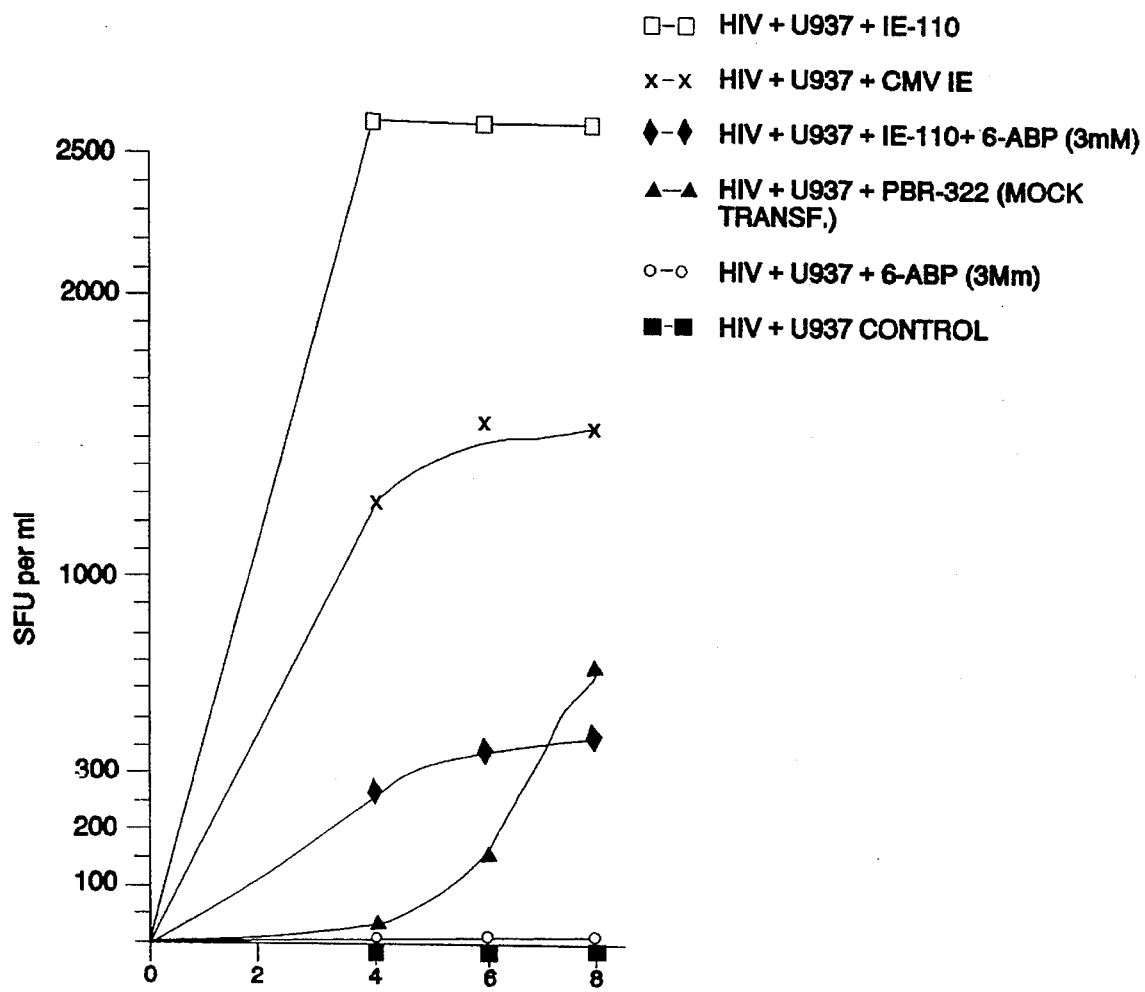
FIG. 3 shows the effect of 6-ABP on HIV activation by co-transfection of HIV with HSV-IE-110 in macrophages (U937 cells).

FIG. 3 illustrates the effect of the drug 6-ABP on HIV activation by cotransfection of HIV with HSV-IE 110 in macrophages (U937 cells). The rationale for taking this approach and the syncytium-forming assay are described in Example 3 with results shown in Table 2. For the purpose of determining the ability of 6-ABP to inhibit HIV growth activation, the duplicate cells cultures were used. In experiments 1 and 2, U937 cells were transfected with HSV IE-110 gene and, CMV IE gene and infected HIV. The viral HIV growth is shown to reach up to and above 2,500 SFU/ml in 4 days for U937 cells cotransfected with IE-110 and to about 1200 to 1400 SFU/ml between 4–8 days for U937 cotransfected with CMV IE. In experiment 3, U937 cells transfected with HSV IE-110 and infected with HIV were treated with 3 mM of 6-ABP. In this combination, the drug treatment was able to suppress the viral growth and reduce HIV activation to background levels of 250–300 SFU per ml between days 4 and 8. Thus, the growth of HIV was inhibited against untreated cultures (experiment 1). Mock transfection of U937 with PBR-322 plasmid shows the early inhibition of HIV growth is followed by growth of HIV up to about 700 SFU/ml during days 4–8. Drug alone (experiment 5) was able to completely inhibit any viral growth. Similarly, there was no HIV growth observed in HIV plus U937 cell cultures without cotransfection or addition of the drug. The results of the 6 experiments are shown in FIG. 3. It is evident that without the activator very little growth of HIV is detectable as evidenced by small differences in slopes of 5 and 6. It is also evident that the drug profoundly depresses IE-110(HSV)-activated growth of HIV as seen in slope 3. CMV-IE-activation is also inhibited by the drug.

Figure 4:
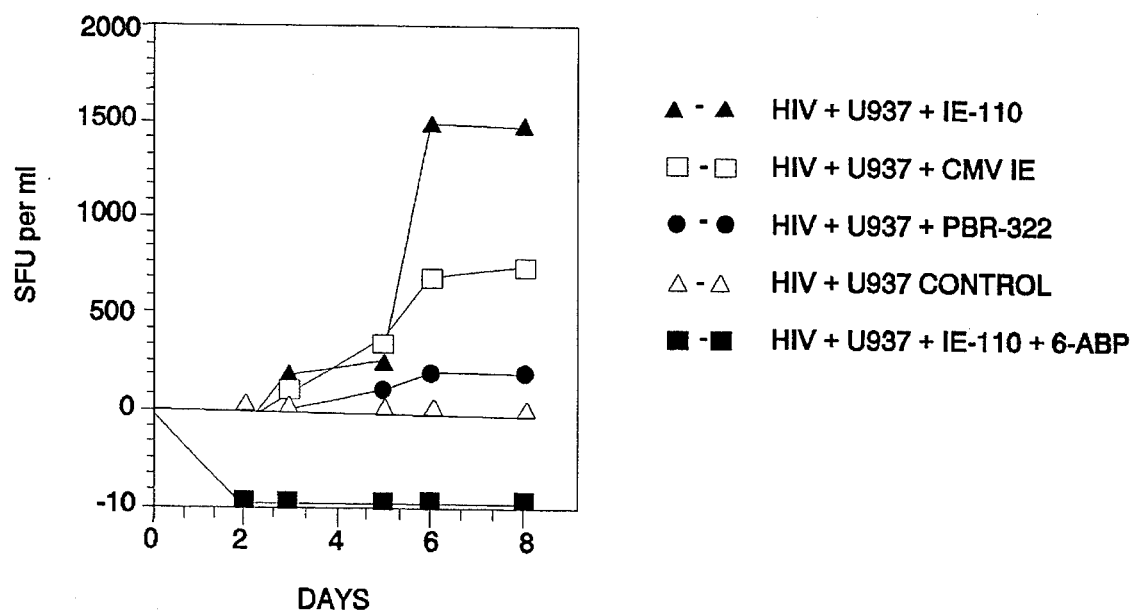
FIG. 4 illustrates the effect of 6-ABP on HIV activation by co-transfection of HIV with lower titre of HSV-IE in macrophages (U937 cells).

In order to assess a possible direct effect of the drug on the growth of HIV, experiments shown in FIG. 3 were reproduced, except that conditions of virus titration (by SFU) were refined, to detect relatively low virus titers. These results, shown in FIG. 4, are essentially identical with those depicted in FIG. 3, except that the assay conditions permit the detection of the effect of the drug on HIV growth alone without the presence of activator. There is a significant effect on HIV growth, indicating that the mechanism of action of the drug appears to involve replication of apparently both the IE-110 and HIV DNA.

In all experiments shown in FIG. 3 and 4, the cells were exposed to 3 mM drug for 24 hrs. However, just as with HSV, the addition of the drug post infection was as effective as when cells were pre-treated. This time, the drug exposure suggests that expression of IE-110 and HIV DNA may be simultaneously inhibited by the drug.

Figure 5:
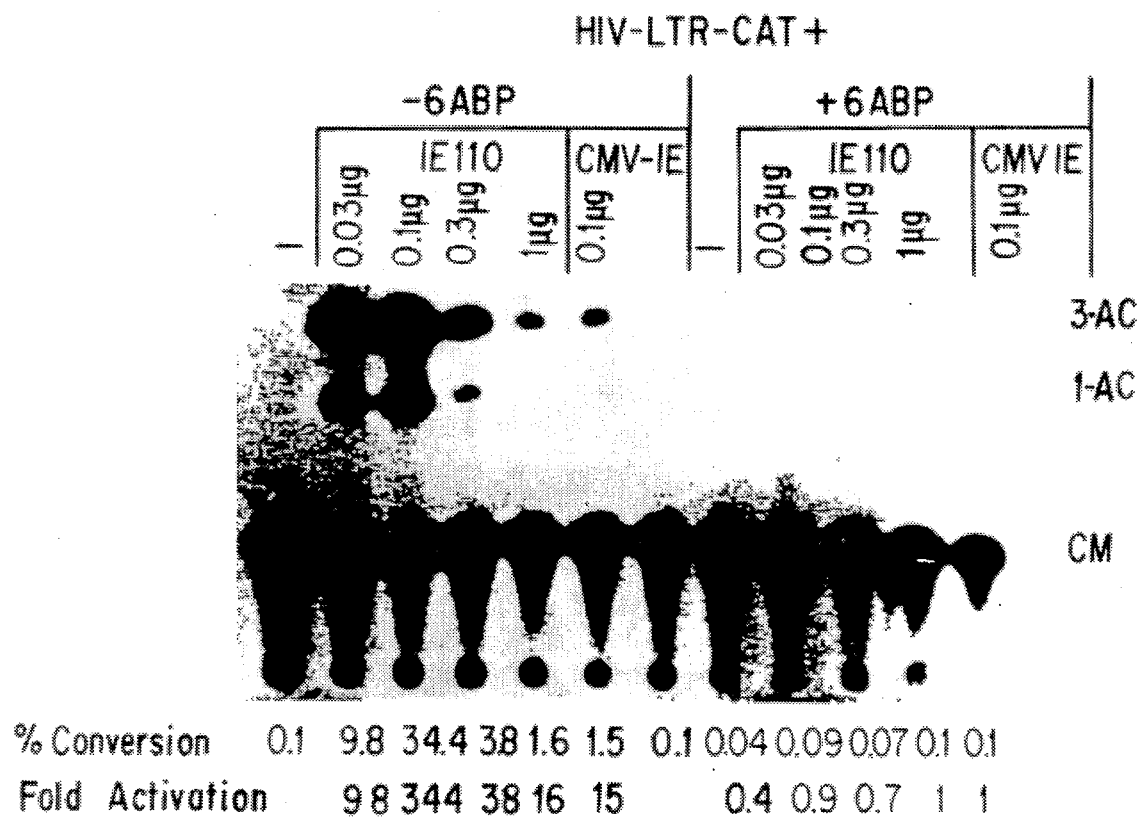
FIG. 5 shows the inhibitory effect of 6-ABP on HIV activation by HSV or CMV as assayed by the HIV-LTR-CAT assay.

Inhibitory effect of the drug on HIV replication as assayed by the HIV-LTR-CAT assay is shown in FIG. 5. IE-110 and CMV-IE titre concentrations were varied from 0.03–1 μg and, as shown in FIG. 5, the maximal activation of HIV-LTR-CAT expression of IE-110 occurred at 0.1 mg concentration where 344-fold activation was observed. This activation was depressed to 0.4–0.9 activation by treatment with 2 mM of 6-ABP.

It is of importance to determine both intracellular drug concentrations and mechanisms of drug transport. Twelve different cell types were incubated with varying concentrations of the drug for varying periods and intracellular drug concentration assayed with the aid of [$5^3$H] labeled 6-ABP. When the testing was done in 12 different established cell lines, it was found that 6-ABP transport was drug-concentration and time of incubation dependent, and that it reached a plateau in 18–24 hours, which plateau was 10–20% of drug concentration applied extracellularly. Thus, there is a significant transport regulation through the cell membrane. The concentration of intracellular drug, with 1 mM extracellular administration varied between 65–200 uM, depending on cell types, but always exceeded the Ki of 6-ABP for ADPRT (47 uM of 195). This shows that specific binding and saturation of ADPRT sites does in fact occur.

Expression of human immunodeficiency virus (HIV) increases after activation of inducer T cells by phorbol esters and lectins as described in *Science*, 108:117 (1948); and Ibid, 230:850 (1986). This stimulation is mediated by NF-kB, a factor that regulates transcription and binds to the twice-repeated 11-bp kB motif in the HIV enhancer *Nature*, 326, 711 (1987). Mutations within this site that eliminate the binding of NF-kB also abolish the increase in HIV gene expression in activated T cells. However, HIV persists in macrophages in which it shows low level of replication.

AIDS disease is associated with high titers of HIV replication. Such high replication suggests that some activation factors are involved in HIV activation in these cells. These observations were published in *Science*, 240:80, (1988) and *Virology*, 167:299, (1988). DNA from primate viruses, including HSV and CMV, induces HIV expression when co-transfected into fibroblasts with a plasmid containing the HIV-promoter linked to the chloramphenicol acetyl transferase (CAT) gene. *Proc. Natl. Acad. Sci.*, 83:9759 (1986). HSV encodes several gene products that activate transcription of other genes. One set of HSV trans-activators is synthesized immediately after infection resulting in immediate-early gene products. These include the trans-activating genes that activate HIV-LTRcat involving induction of NF-kB activity. CMV also activates HIV expression. This is mediated by the CMV IE gene. However, it does not appear to require NF-kB activity.

Figure 6:
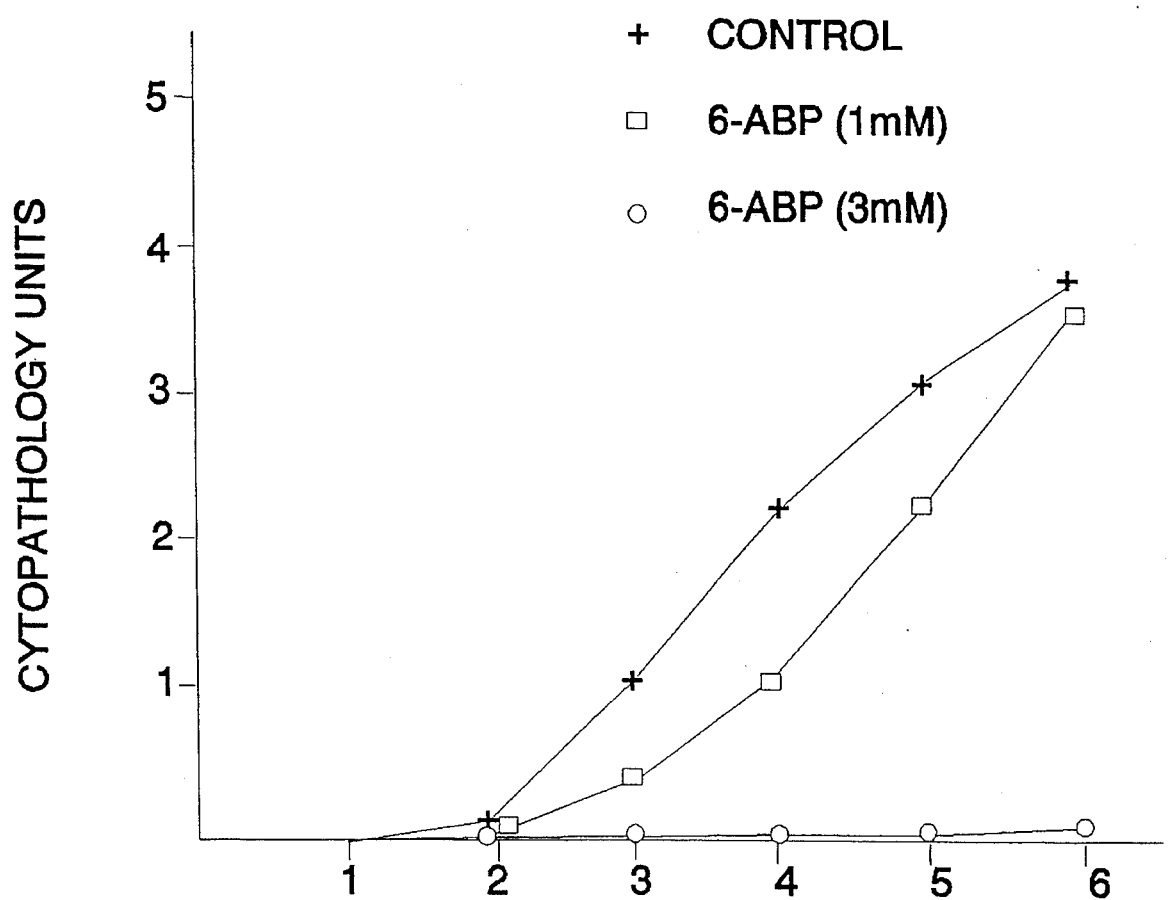
FIG. 6 shows the effect of extracellularly applied 6-ABP on the time course of HIV propagation.
Figure 7:
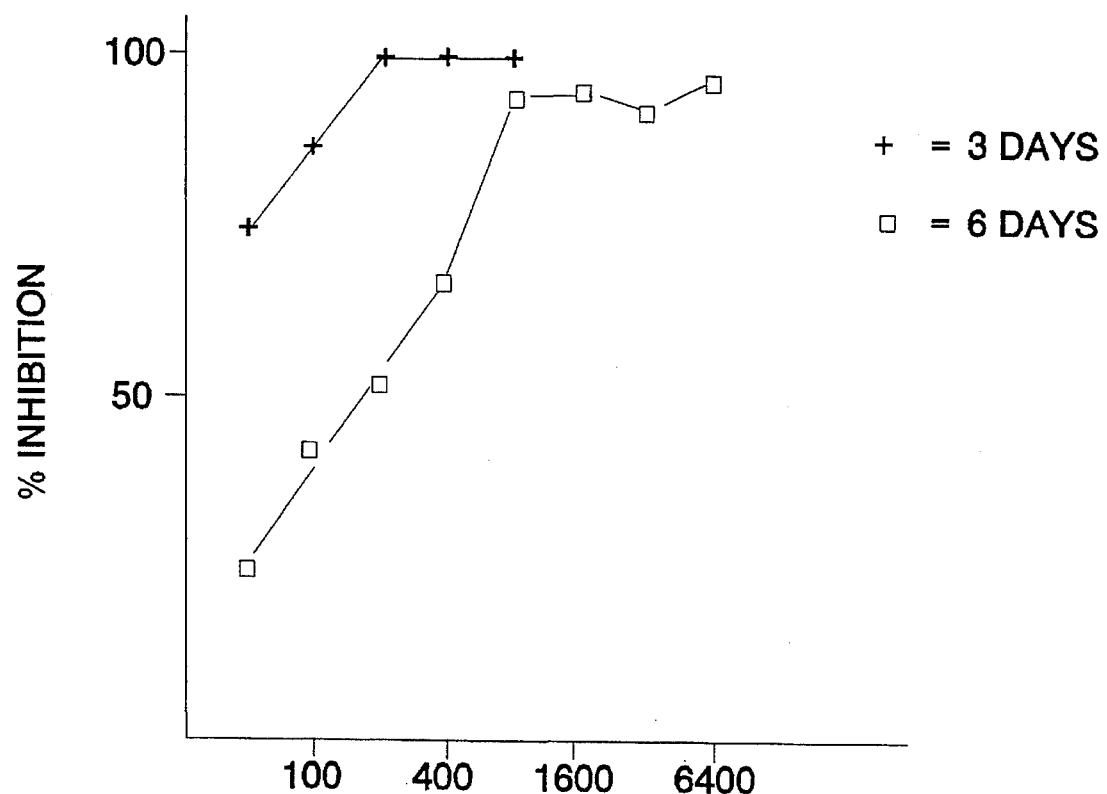
FIG. 7 shows the effect of 6-ABP on HIV growth inhibition in AA-2 cells.

Experiments were performed to determine the direct effect of 6-ABP against HIV in established cell culture. The results are shown in FIGS. 6 and 7 and in Table 4. These results show the effect of 6-ABP on direct propagation of highly virulent HIV strain in MOLT III cells, using as a source of virus the MOLT III cell supernatant on AA-2 and MT2 cells in culture.

Whereas the activation of latent HIV by various DNAs and its prevention by 6-ABP were shown above, the following experiments examine the effects of 6-ABP on the direct propagation of highly virulent HIV strain obtained from NIH in Molt III cells, using cell supernatant as source of virus on AA-2 and MT2 cells in culture. More than 60 tests were performed varying virus titers, time of exposure, and exposure to 6-ABP.

It is not known whether the rate of conversion of the drug (6-ABP) to its active metabolite 6-nitroso-1,2-benzopyrone (6-NBP) is dependent on the rates of penetration of 6-ABP into the cell and on the rates of conversion of 6-ABP to 6-NBP by oxygenation in the cell. Therefore, the extracellular drug concentration is only indirectly related to biological action which depends on the intracellular generation of 6-NBP. This consideration is valid for all cell culture type experimentation.

As seen from FIG. 6, the effect of 6-ABP greatly increases between 1 mM and 3 mM of external drug concentration, which reflects two biological parameters that are characteristic for every cell type, namely the drug preservation, and oxygenation catalysis. It is apparent that, at fixed initial virus concentrations, assayed by cytopathogenicity test, 3 mM 6-ABP completely eliminates HIV propagation even at day 6 while the 1 mM 6-ABP is able to suppress the HIV propagation only slightly against controls.

FIG. 6 shows the effect of two concentrations of externally, i.e. extracellularly, applied 6-ABP on the time course of viral propagation in AA-2 cells in culture. The effect of 1 and 3 mM 6-ABP on the rate of HIV propagation is assayed by cytopathogenicity at a fixed HIV dilution 1:1600.

FIG. 7 illustrates the effect of 3 mM 6-ABP on HIV growth inhibition in AA-2 cells after 3 days and 6 days. The culture was exposed to 3 mM of the drug at varying HIV dilutions. 6-ABP concentration acting for 3 or 6 consecutive days on AA-2 cells is depicted as a function of virus concentration (given as HIV dilution on the abscissa). The drug effect, as predictable—varies in magnitude from 70% to 100% inhibition at 3 days or 25 to 100% in 6 days as a function of virus concentration clearly demonstrates that 6-ABP, or rather its 6-NDP metabolite is an effective anti HIV-agent.

Figure 8:
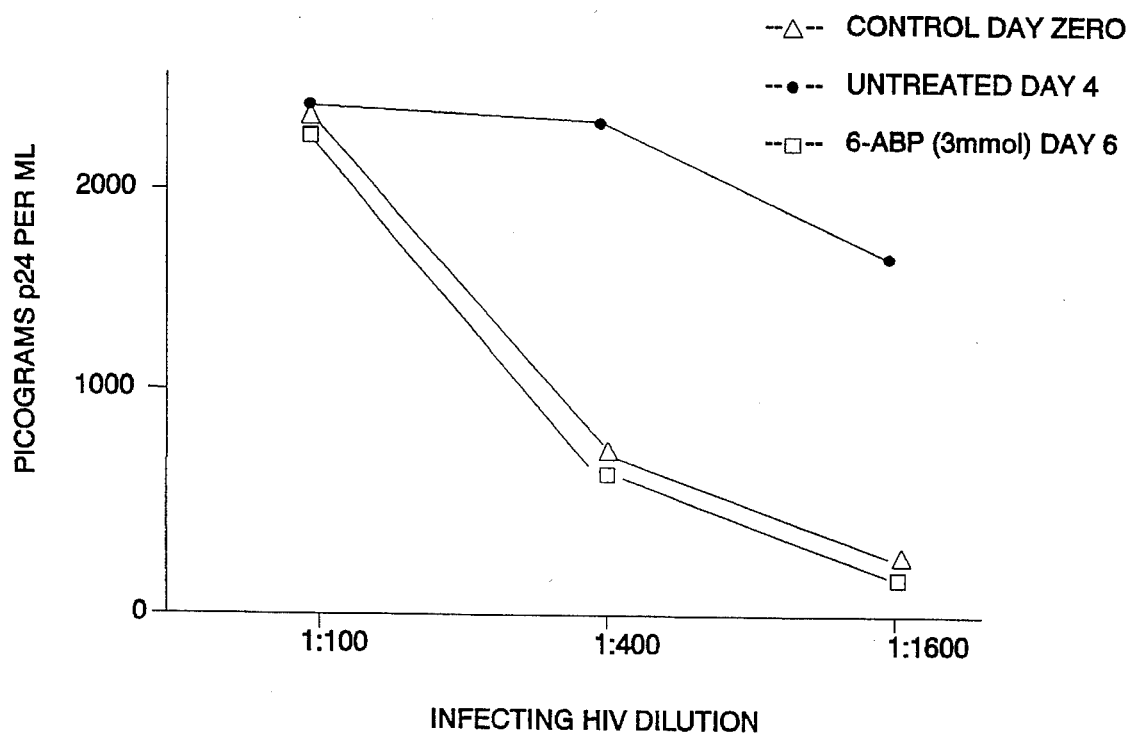
FIG. 8 shows the effect of 6-ABP on HIV replication followed by the conventional analysis of p 24 formation.

The effects of 3 mM 6-ABP on HIV replication in AA-2 cells using the same experimental set-up as for FIG. 7 was followed by the conventional analysis of p 24 formation by automated ELISA tests. The results are shown in FIG. 8, where as in FIG. 7, the influence of varying HIV concentrations infecting HIV dilution, from 1:100 to 1:1600 or p 24 input, as shown in graph, was monitored.

3 mM 6-ABP was effective as anti-HIV drug. At day 4, 3 mM 6-AB completely suppressed p 24 generation at 1:1400 dilution and profoundly inhibited HIV replication beyond a virus dilution of 1:1400.

Figure 9:
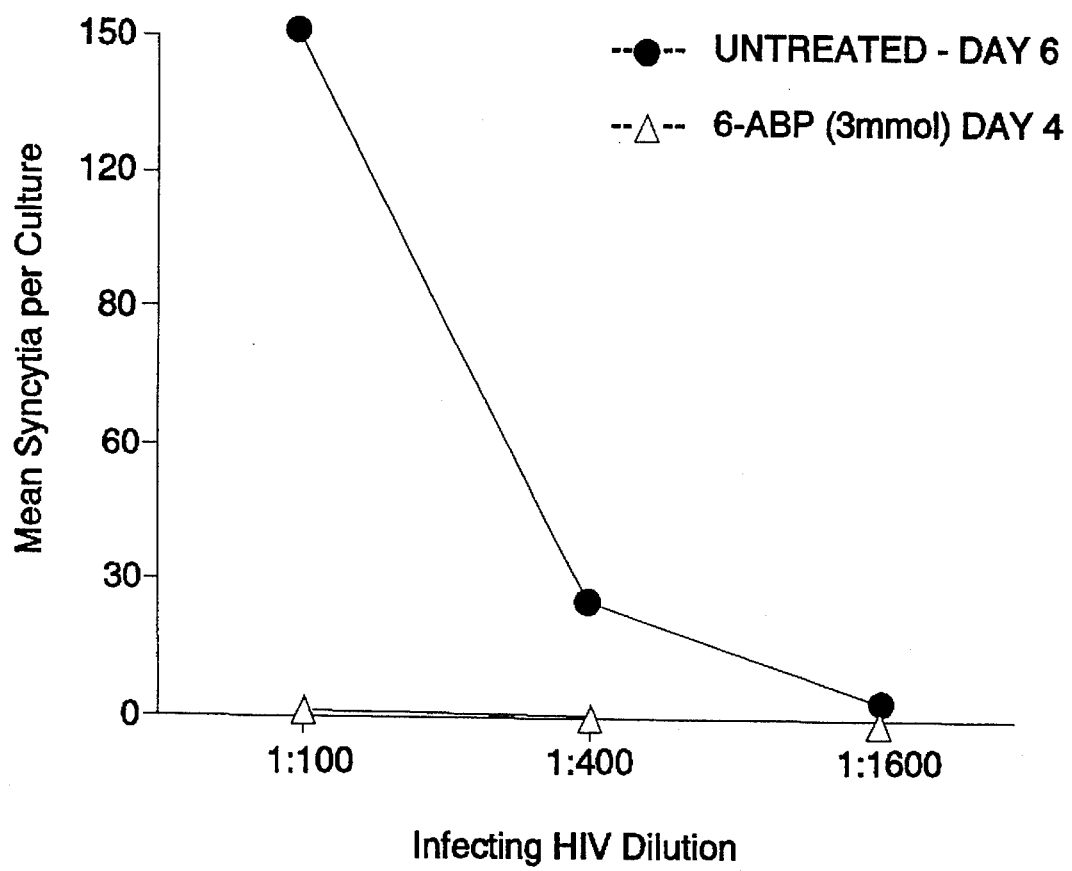
FIG. 9 shows the inhibitory effect of HIV reproduction and syncytia formation in MT-2 cells.

Equivalent results, shown in FIG. 9, were obtained with MT-2 cells. In FIG. 9, the inhibition of syncytia formation was quantitatively assayed. From FIG. 9, it is apparent that 3 mM 6-ABP nearly completely suppressed HIV production, as evidenced by the almost complete inhibition of syncytia formation. At very high HIV titre, at 1:100 dilution the untreated syncitia formation was 150 times higher than in treated culture.

Results exemplified in FIGS. 6, 7, 8, 9 and Table 4 were reproduced in nearly 30 series of experiments and consistent antiviral effectivity of 6-ABP was obtained.

The antiviral testing of drugs in established cell cultures, while producing highly significant and reproducible results, have the inherent problem of dealing with somewhat modified cells due to culturing, immortalization, metabolic alterations, etc. Thus, direct correlation with the human disease must take into account possibly altered cell membrane permeability and cyt p 450 content, which are critical parameters in evaluating the medical effectivity of 6-ABP and its derivatives.

Such correlation was with lymphoblasts obtained from human AIDS patients. The results are shown in FIG. 10 and FIG. 11.

Figure 10:
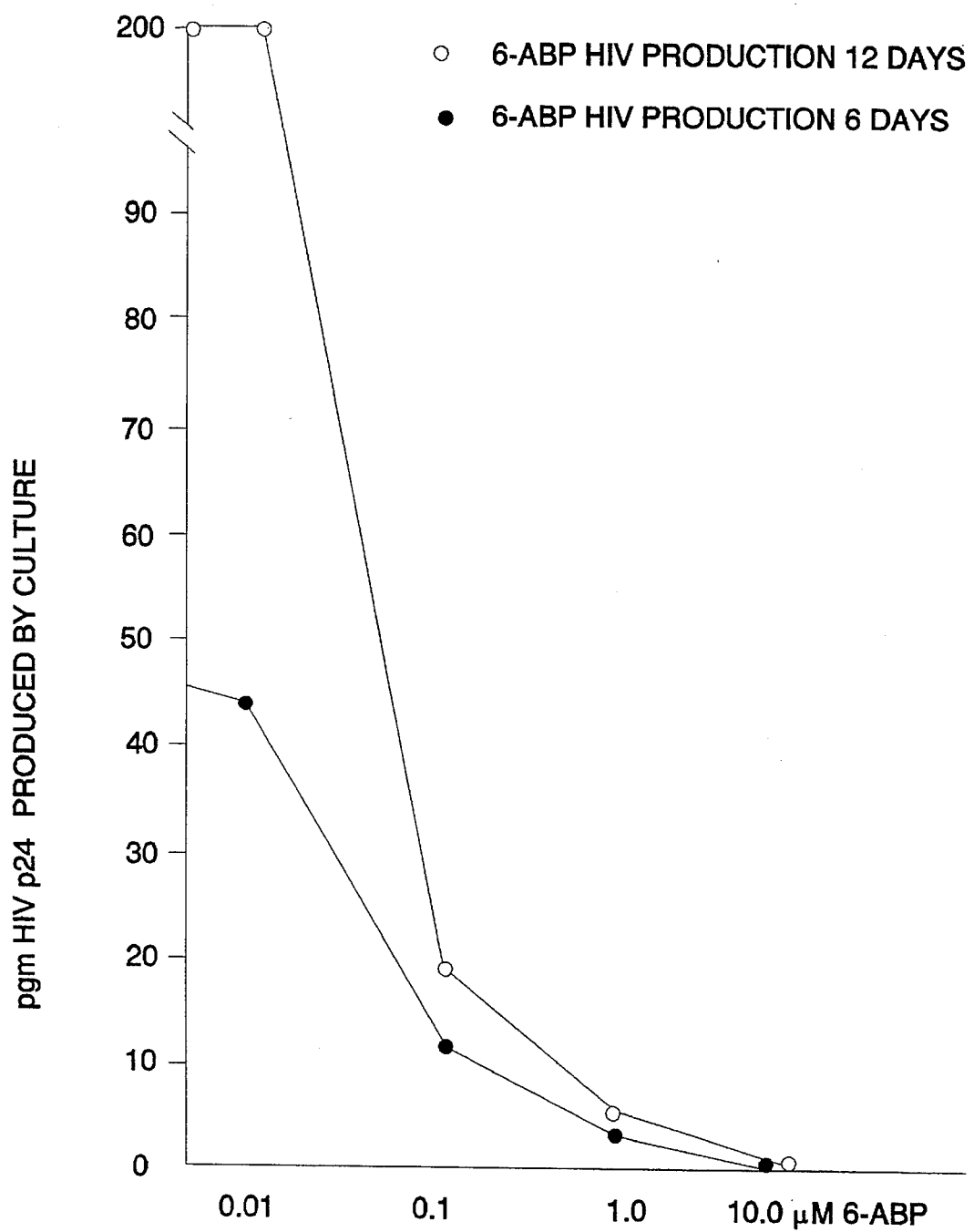
FIG. 10 shows the inhibitory effect of 6-ABP on HIV proliferation in human lymphoblasts from AIDS patients.

In FIG. 10, human lymphoblast exposed to 6-ABP for 18 hours. The drug concentrations studied were between 0.01 to 10 mM. HIV production was studied in two time intervals, 6 and 12 days after the drug removal. At both 6 and 12 days, HIV production decreased dramatically at treatment with 0.1 µM 6-ABP, showing that a very low concentration (0.1 µm) of 6-ABP is sufficient to substantially inhibit the HIV proliferation in AIDS lymphoblasts.

FIGS. 11A through 11E illustrates the selective inhibition of HIV replication without effecting DNA synthesis of lymphoblasts. FIGS. 11A through 11E shows that 6-ABP does not influence genomic DNA synthesis after 18 hours exposure.

Figure 11A:
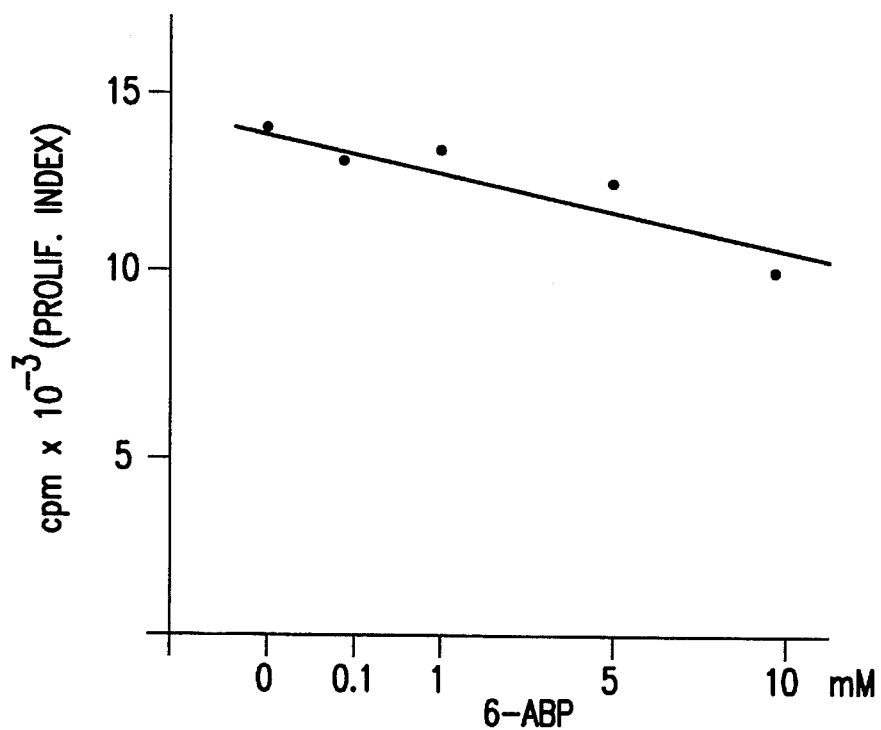
FIGS. 11A, 11B, 11C, 11D and 11E shows the selective inhibition of HIV replication by 6-ABP.
Figure 11B:
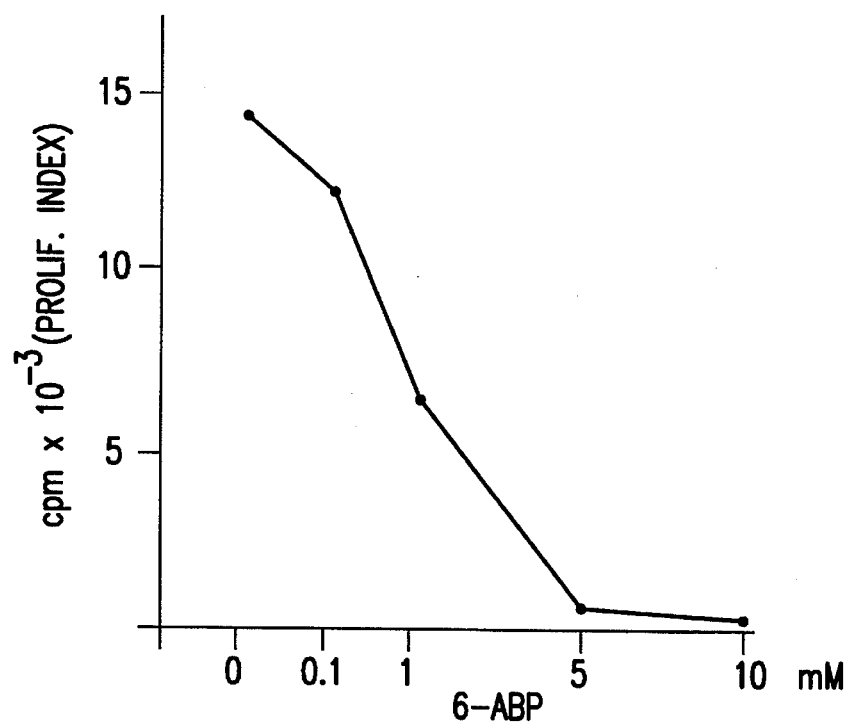
Figure 11C:
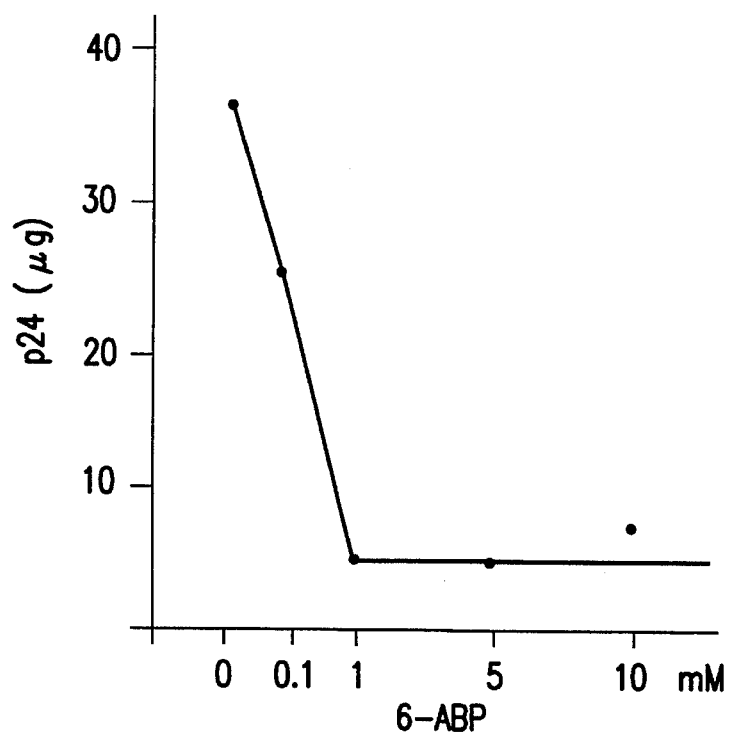
Figure 11D:
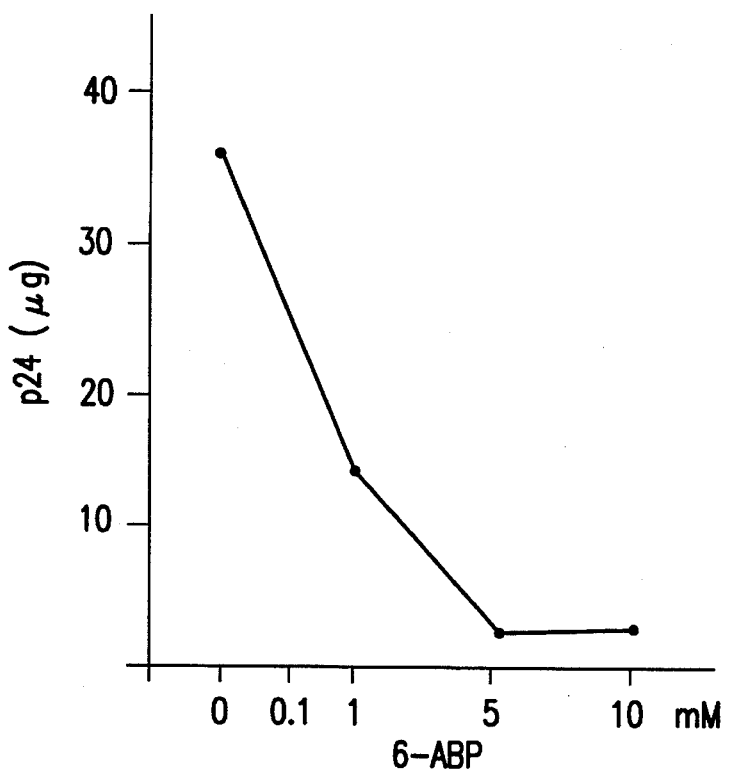
Figure 11E:
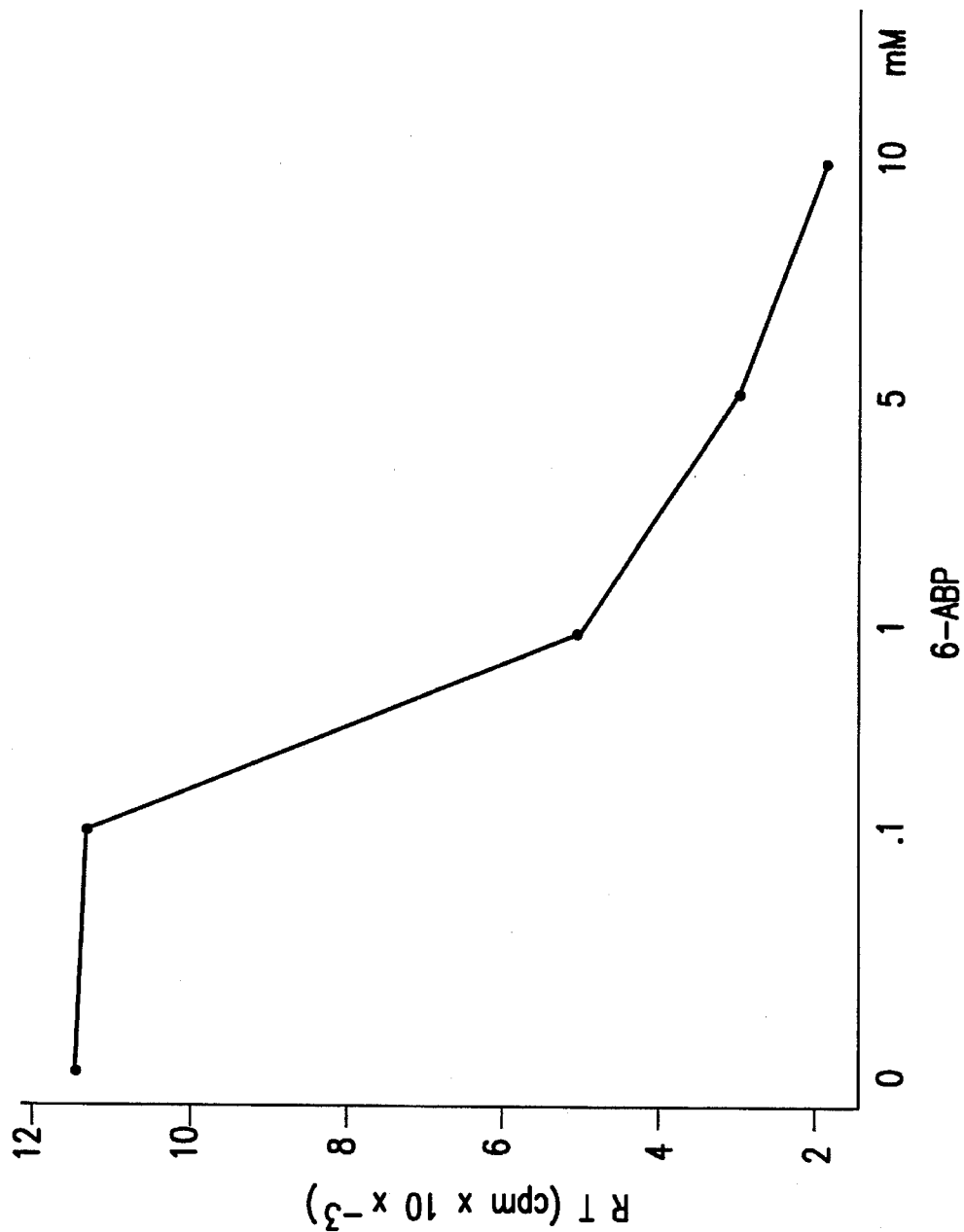

In FIGS. 11A through 11E, normal lymphoblasts stimulated with PHA are infected with HIV and at the same time are submitted to various concentrations from 0–10 mM 6-ABP. After the short exposure of 18 hours, both HIV and 6-ABP are removed, FIGS. 11A, 11C, 11E and the 6-ABP in the same concentrations is readded up to 4 days to cultures shown in FIGS. 11B and 11D. At 4 days, proliferation index measured by $^3$H-thymidine incorporation is determined in FIGS. 11A and 11B. As seen from FIG. 11A, 18 hours treatment with 6-ABP did not effect the DNA synthesis measured by cell proliferation. In FIG. 11B, where the cell culture was exposed to additional 6-ABP treatment, HIV is inhibited and the synthesis of DNA is temporarily also inhibited. In FIGS. 11C and 11B, the viral synthesis or inhibition is measured by p 24 assay. For both FIGS. 11C and 11D cultures, the viral multiplication was almost completely inhibited. The above results were confirmed in FIG. 11E, wherein the reverse transcriptase assay was used to show the virus inhibition.

It is known that white blood cells have efficient $O_2$ generating system. Thus, the conversion of 6-ABP to 6-NBP occurs much more efficiently in white blood cells than in adapted cell cultures. Hence the conversion of the pro-drug 6-ABP to the active species is much higher and thus, it has greater chemotherapeutic activity. Therefore, 6-ABP will be particularly highly effective in patients suffering from AIDS, if treated by intravenous infusion which mode of administration avoids the fast metabolic conversion of 6-ABP to 6-NBP in liver and its reconversion ot 6-ABP by glutathione dependent futile (inactivating) cycle.

Results shown in FIG. 10 were essentially reproduced in whole blood of HIV infected patients, thus clinical effectivity appears measurably assured.

The finding that 6-ABP inhibits HSV growth implies that ADPRT is involved in virus replication. Two more series of experiments were done in order to clarify this question. The results are shown in FIG. 12 and in Example 6.

Figure 12:
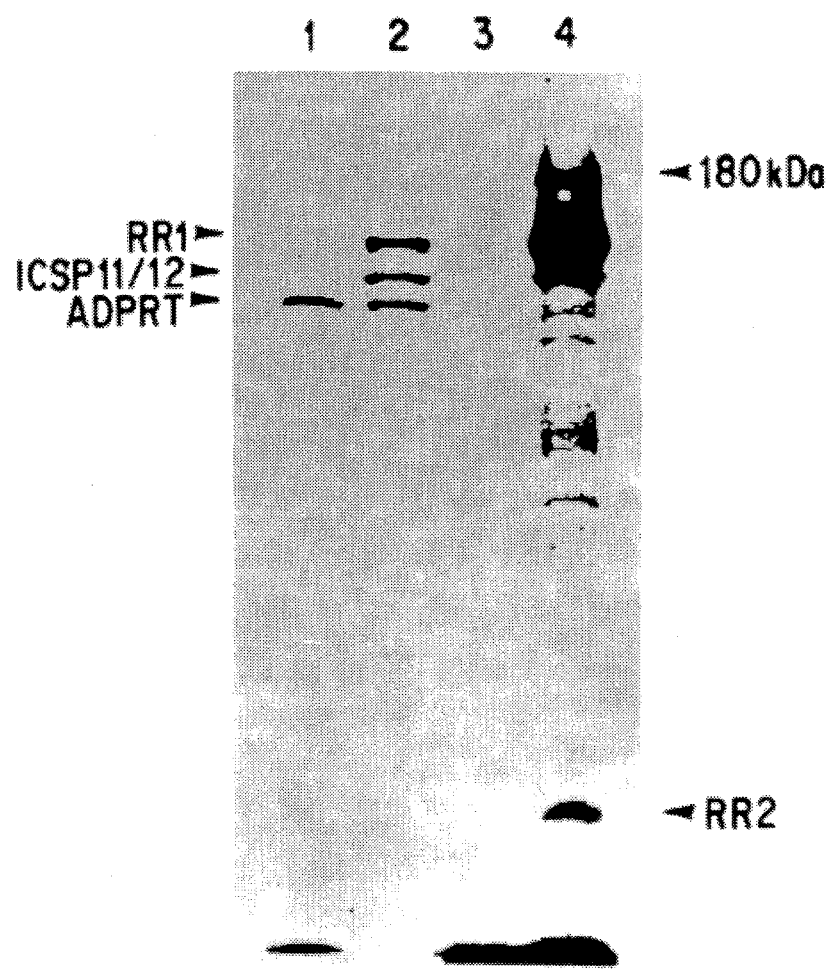
FIG. 12 shows the SDS' gel of HSV proteins RR, and ICSP11/12 which are coprecipitated with ADPRT by anti-ADPRT antibody.

In the first series illustrated in FIG. 12, antibody to ADPRT was used in immunoprecipitation experiments designed to determine the relationship, if any, between ADPRT and viral proteins involved in DNA replication. In these experiments HEp-2 cells were infected with HSV-2 and labeled with $^{35}$S-methionine at 0 to 12 hours post infection. Extracts were prepared and immunoprecipitated with antibody to ADPRT using previously described procedures in *J. Virol.*, 63:3389 (1989). Ribonucleotide reductase is one of the enzymes involved in viral DNA synthesis and its expression is required for virus growth. Therefore, as control for the anti-ADPRT antibody, an antiserum to a synthetic peptide (LA1) was used that consists of 13 amino acid residues in the large subunit of the HSV-2 ribonucleotide reductase (RR1). Early after HSV-2 infection, the LA1 antibody was shown to precipitate only the HSV RR1. Later in infection when the small subunit of HSV ribonucleotide reductase (RR2) is synthesized, the LA1 antibody also precipitates RR2 and a 180kDa, as yet uncharacterized cellular protein both of which are complexed with RR1. This is shown in FIG. 12, Lane 4. LA1 antibody does not precipitate any proteins from uninfected cells similarly labeled are processed (FIG. 12, Lane 3). Antibody to ADPRT precipitates ADPRT from uninfected cells (FIG. 12, Lane 1). From HSV infected cells (FIG. 12, Lane 2) it precipitates ADPRT as well as RR1 and ICSP11/12, the major HSV DNA binding protein that is involved in DNA unwinding and replication.

These data indicate that ADPRT is complexed with HSV proteins that are involved in HSV replication thereby contributing to virus growth.

UTILITY 6-amino-1,2-benzopyrones are potent, specific and nontoxic antiviral drugs which selectively inhibit the virus reproduction in viruses such as HIV, HSV and CMV. Consequently, these drugs are useful for treatment of viral diseases caused by these viruses, namely for treatment of AIDS, herpetic lesions and cytomegalovirus infection. It is expected that other viral diseases will also be susceptible to treatment with 6-ABP.

In the practice, the compound of this invention, namely substituted or unsubstituted 6-ABP of formula I or any of its pharmaceutically acceptable salt, will be administered in amount which will be sufficient to inhibit the viral expression in the host cell and in the pharmaceutical form most suitable for such purposes.

Administration of the active compounds and salts described herein can be via any of the accepted modes of administration for therapeutic agents. These methods include systemic or local administration such as oral, parenteral, transdermal, subcutaneous, or topical administration modes. The preferred method of administration of these drugs is intravenous, except in those cases where the subject has topical lesions, such as HSV lesions and sores, where the topical administration may be proper. In other instances, it may be necessary to administer the composition in other parenteral or even oral forms.

Depending on the intended mode, the compositions may be in the solid, semi-solid or liquid dosage form, such as, for example, injectables, tablets, suppositories, pills, time-release capsules, powders, liquids, suspensions, or the like, preferably in unit dosages. The compositions will include an active 6-ABP compound of formula I or the pharmaceutically acceptable salt thereof, and in addition, it may include any conventional pharmaceutical excipients and other medicinal or pharmaceutical agents, carriers, adjuvants, diluents, etc.

The amount of active compound administered will, of course, be dependent on the subject being treated, on the subject's weight, the severity of the affliction, the manner of administration and the judgment of the prescribing physician. However, an effective dosage is in the range of 0.01 to 5000 mg/kg/day, preferably 0.1 to 1000 mg/kg/day, more preferably 1 to 100 mg/kg/day. The upper limit of course is when the patient shows toxic effects. However, since the compounds of this invention are practically non-toxic, the administered dose may be as high as needed.

For solid compositions, in addition to the active 6-ABP compound of formula I, such excipients as for example, pharmaceutical grades of mannitol, lactose, starch, magnesium stearate, sodium saccharin, talcum, cellulose, glucose, sucrose, magnesium carbonate, and the like may be used. The active 6-ABP compound I, as defined above, may be also formulated as suppositories using, for example, polyalkylene glycols, for example, propylene glycol, as the carrier.

Liquid, particularly injectable compositions can, for example, be prepared by dissolving, dispersing, etc. an active 6-ABP compound I in a pharmaceutical solution such as, for example, water, saline, aqueous dextrose, glycerol, ethanol, and the like, to thereby form the injectable solution or suspension.

Parenteral injectable administration is generally used for subcutaneous, intramuscular or intravenous injections and infusions. Injectables can be prepared in conventional forms, either as liquid solutions or suspensions or, solid forms suitable for dissolving in liquid prior to injection.

A more recently devised approach for parenteral administration employs the implantation of a slow-release or sustained-released systems, which assures that a constant level of dosage is maintained. See, e.g., U.S. Pat. No. 3,710,795, which is incorporated herein by reference.

Normally, 6-ABP would not be effective per os because of the rapid detoxification of the nitroso derivative in the liver, however, appropriate chemical modification of 6-ABP as simultaneous administration of glutathion depressing drug which would prevent such rapid metabolism in the liver is contemplated to be developed and is, as all other possible pharmaceutical compositions within the scope of this invention.

If desired, the pharmaceutical composition to be administered may also contain minor amounts of nontoxic auxiliary substances such as wetting or emulsifying agents, pH buffering agents, and the other substances such as for example, sodium acetate, triethanolamine oleate, etc.

Actual methods of preparing such dosage forms are known, or will be apparent to those skilled in this art, and are in detail described in *Remington's Pharmaceutical Sciences*, Mack Publishing Company, Easton, Pa., 17th Edition, 1985. The composition or formulation to be administered will, in any event, contain such quantity of the active compound(s) which will assure that a therapeutically effective amount, will be delivered to a patient. The therapeutically effective amount means an amount effective to prevent development or to alleviate the existing symptoms of the subject being treated.

Any of the pharmaceutical compositions may contain 0.1–99% of the active 6-ABP ingredient, preferably 1–70%.

On the basis of the knowledge of fairly detailed mode of action of 6-ABP it is possible to formulate predictions regarding its medicinal usefulness.

6-ABP, preferably in the form of any of its pharmaceutically acceptable salt, such as for example the hydrochloride, is a reasonably well soluble molecule in aqueous media. It can form 10–12 mM solution at pH 7.2–7.9, which is stable for months at room temperature, if kept in the dark with only trace (less than 0.10%) decomposition. Such solution would be reasonably stable for use as an intravenous infusion formulation. The intravenous infusion is the most likely effective mode of administration against HIV at any stage of the disease. Since 6-ABP is known to cross the blood brain barrier, it will be useful for treatment of AIDS neurological disorders. 6-ABP is also effective for treatment of AIDS related Kaposi's sarcoma of inner organs. Properly formulated, it will also effect skin disorders.

In AIDS patients about 1 g of 6-ABP/average body infusion weight typically provides effective chemotherapy. The chemotherapy may be repeated intermittently while HIV is or even when it is not detectable.

Moreover, due to its non-toxicity, the 6-ABP therapy may be provided alone or in combination with other antiviral or other drugs, such as for example AZT, antibiotics, corticosteroids, vitamins and other drugs. There are no contraindications to use 6-ABP with AZT, other drugs even such toxic drug as since modes of action are quite different and possible synergism between 6-ABP and other drugs is predictable.

6-ABP compounds are equally useful for treatment of herpetic lesions caused by both HSV-1 and HSV-2. The drug would be preferably administered by i.v. infusion or other parenteral or systemic mode of administration. In case of sores, the drug could be also administered topically. Infection caused by CMV would be treated preferably in the same fashion as that suggested for AIDS treatment.

One primary advantage of the 6-ABP is the absence of toxicity. Since the drug is acting very specifically only on the enzyme ADPRT responsible for viral reproduction and is not acting on any other enzyme, it does not have any undesirable side effects.

In absence of any side effect and toxicity, the drug may be advantageously used not only for the treatment of existing HIV, HSV and CMV or other viral infections, but also for a prevention of such infections. It may also be preventively administered in cases of lowered immunoresistance to prevent development of secondary viral infections.

Substituted 6-ABPs, containing substitution on $R_1$–$R_5$ which produce more lipophilic molecules render pharmaceuticals that more readily penetrate the cell wall and may have even more higher efficiency than 6-ABP, and thus may be more effective at lower concentrations.

The following preparations and examples serve to illustrate the invention. They should not be construed as narrowing it, or limiting its scope.

Various substituents of 6-ABP (as shown in formulae) are likely be modify lipid solubility rate of cellular penetration, thus clinical dosage schedules but the above biochemical mechanism is not likely to be altered on a molecular level by substituents.

METHODS AND MATERIALS

Virological Methods

Cells and Viruses

Vero (African green monkey kidney) and MRC-5 (human lung fibroblast) cells (M.A. Bioproducts, Walkersville, Md.) were grown in Eagle's minimal essential medium (MEM) with 25 mM Herpes buffer and 10% fetal bovine serum (FBS). Human epidermoid carcinoma No. 2 (HEp-2) cells were grown in medium 199 with 10% FBS. Rhesus monkey kidney (RMK) cells obtained commercially from M.A. Bioproducts, were grown in Eagle's MEM and maintained with 2% FBS. U937 human monocytic cells were grown in RPMI with 10% FBS and 1% sodium pyruvate. MT2, T cell leukemia cells originally obtained from NIH, were grown in RPMI 164 with 10% FBS.

Herpes simplex virus (HSV) type 1 and 2 (F and G strains, respectively) were grown in HEp-2 cells and titered by plague assay under liquid overlay as described in *Proc. Natl. Acad. Sci.*, 83:2787 (1986).

Adenovirus, Respiratory Syncytium virus (RSV), Influenza virus, Enterovirus and Cytomegalovirus (CMV) were original patient isolates obtained in clinical service. CMV was grown in MRC-5 cells in MEM with 10% FBS, RSV in HEp-2 cells in MEM with 2% FBS, Adenovirus, Influenza and Enterovirus in RMK cells in MEM with 0.8% Bovine serum albumin (Fraction V) and 25 mM Herpes buffer (influenza) or 2% FBS (Adenovirus, Enterovirus). HIV-1 was originally obtained from NIH and grown in Molt 3 cells.

Virus Titers for CMV and RSV

Adenovirus and Enterovirus are expressed as the highest dilution that causes 50% cytophatic effect (TCID50). Virus titers for HSV-1 and HSV-2 are expressed as syncytial forming units (PFU) per ml. HIV titers are expressed as syncytial forming units (SFU per ml), assayed on MT2 cells. Influenza virus is titrated by hemagglutination and titers are expressed as the highest dilution that caused 50% hemagglutination. In this assay, tubes containing infected RMK cells are exposed for 1.5 hrs. at 4° C. to a 0.5% suspension of guinea pig red blood cells in Hank's Balanced salt solution, washed and read for adhering cells.

Plasmids

All chimeric CAT constructions were prepared in pCATB' containing the CAT structural gene without eukaryotic promoter sequence. The target location of the virus sequences in plasmids pXhoIC and pIGA15 that respectively contained the genes for the IE175 and IE110 proteins of HSV-1 have been described *J. Virol*, 63:2773 (1989).

DNA Transfection

DNA transfection was performed with DEAE dextran. Briefly, U937 cells (5×10$^6$) were exposed for 60 min. at 37° C. to a mixture of DEAE Dextran (1.05 ug/ml) and DNA in STBS buffer (25 mM Tris HCl, having pH 7.5, 137 mM NaCl, 0.5 MgCl$_2$, 0.7 mM CaCl$_2$ and 5 mM KCl and 0.6 mM Na$_2$HPO$_4$) in 15 ml snap cap 6×35 mm polyethylene dishes from Costar, Cambridge, Mass., at 5×10$^6$ cells per well. Routinely, transfection mixtures contained 1.0 ug of target supercoiled plasmid and 0.1 ug DNA to equalize nucleic acid concentration effects. Transfected cells were harvested 40 to 44 hr post transfection in CAT harvest buffer (40 mM Tris, having pH 7.4 150 mM NaCl, 1 mM EDTA) and stored at −20° C. until assayed.

CAT Assays

All harvesting and CAT assays were performed as described in *J. Biol. Chem.*, 263:1505 (1988). Routine assay conditions employed 0.2 uCi of [$^{14}$C]-chloramphenicol substrate and an incubation time of 60 min. For quantitative estimates of CAT activity and fold activation, the appropriate sections were cut from the thin-layer chromatography scintillation fluid added and the radioactivity was counted in a scintillation counter. Quantitative comparisons were made by measuring the amounts of chloramphenicol-acetate product with enzyme concentrations and time. pSV CAT was used as a positive control, and the parent (pCATB') was used as a negative control.

EXAMPLE 1

Preparation of 6-Amino-1,2-Benzopyrones

This example illustrates the preparation of 6-amino-1,2-benzopyrones.

Preparation of 6-amino-1,2-benzopyrones

The method employed to prepare 6-ABP is a modification of a published procedure in *J. Heterocylic Chem.*, 23:87 (1968).

In a fume hood, to 0.50 g of 10% palladium catalyst on activated carbon suspended in 30 ml of water in a 125 ml flask a solution of potassium borohydride (2.70 g., 0.050 mole) in 35 ml of water was slowly added. The combined mixture was then transferred to a 2-liter flask equipped with a magnetic stirrer and a solution of commercial 6-nitro-1, 2-benzopyrone (3.82 g., 0.020 mole) in 1000 ml of methanol was gradually added at room temperature. After addition was compete the mixture was stirred for 15 minutes more, suction filtered through Celite on a Buchner funnel to remove the catalyst and stripped of methanol by rotary evaporation. The residue was collected by suspending it in cold water and pouring onto a Buchner funnel. After drying, the material was recrystallized from ethanol to give 2.18 g (68% yield) of the yellow product, m.p. 166°–169° C. Mass spectrum: 161 (M+), 133, 104, 78, 52. and/or by introducing modifications as described in the Preparation Procedures.

Preparation of 6-amino-1,2-benzopyrone hydrochloride

To a stirred suspension of 6-amino-1,2-benzopyrone (1.61 g., 0.010 mole) in 20 ml of water was added 2M aqueous hydrochloric acid dropwise until the amine was dissolved (pH 3–4). The solution was then filtered and stripped of water by rotary evaporation and vacuum pumping. The dry residue was then taken up in hot absolute methanol, treated with activated decolorizing to give light yellow crystals of the hydrochloride salt (1.60 g., 81% yield), m.p. 280°–285° C. (with decomposition). Mass spectrum: 161 (M-HCl)+, 133, 104, 78, 52, 51.

Other salts are prepared by the same or similar procedure substituting the hydrochloric acid with other suitable acids.

EXAMPLE 2

Effectivity of 6-ABP Against HSV and CMV

This example illustrates the inhibitory activity of 6-ABP on HSV and CMV replication in a cell culture infected either with HSV or CMV.

Vero, HEp-2 of MRC-5 cells were exposed to various concentrations from 0.1 to 10 mM of 6-ABP in various intervals before (24 hours), during (0 hr) or after (4 hours) infection with HSV-1 or HSV-2 (5–10 PFU/cell), and virus titers were determined 24 hours later.

The results already discussed in FIGS. 1A, 1B, 2A and 2B show that when treated before, during and after the infection 6-amino-1,2-benzopyrone (6-ABP) inhibited both HSV and CMV growth.

Addition of 6-ABP at 24 hours before infection caused a dose-dependent decrease in HSV-1 or HSV-2 titers. In both cases, HSV-2 was significantly more sensitive than HSV-1. Thus, additions of 1 mM 6-ABP caused 50% inhibition of HSV-1 growth while 90% inhibition of HSV-2 growth was observed in cells treated with 1 mM 6-ABP. The inhibition did not increase significantly in cultures exposed to higher than 10 mM 6-ABP concentrations, showing that 10 mM dose was sufficiently light to inhibit significantly the viral growth.

6-ABP treatment at the time of infection (0 hours) or at 4 hours post infection caused essentially similar inhibition patters; 85% and 72% inhibition of HSV-2 growth was observed in cells treated with 1 mM 6-ABP at 0 and 4 hours post infection, respectively. Inhibition did not significantly increase in cells similarly treated with 10 mM 6-ABP. Consistent with the findings from 24 hours pretreated cells, the inhibitory effects on HSV-1 growth were somewhat lower in cells treated with 1 mM 6-ABP at 0 and 4 hours post infection resulting in 60–65% inhibition respectively. The inhibition was approximately 80% in cells treated with 10 mM 6-ABP. These data indicate that 6-ABP exerts a significant inhibitory effect on HSV-1 and HSV-2 growth in cells pretreated or treated with as little as 1 mM 6-ABP. Inhibition is still observed when cells are treated as late as 4 hours post infection, when most of the early virus functions leading to virus replication have already expressed.

The inhibitory effect of 6-ABP is not affected by cell type, as essentially identical results were obtained in studies comparing virus growth in HEp-2, Vero and MRC-5 cells.

The same studies as described above were done using CMV infected cell culture. As shown in Table 1, 6-ABP treatment also effectively inhibits CMV growth. However, in studies where other viruses such as RSV, Influenza virus, Adenovirus and Enterovirus was submitted to 6-ABP treatment, such treatment appears to have no effect on RSV, Influenza virus, Adenovirus and Enterovirus growth, as shown in Table 1.

In this experiment, cells were exposed to 1 mM 6-ABP for 24 hours and infected. Virus titer were determined at the time of maximal CPE. Enterovirus was ECHO-11.

TABLE 1

Effect of 6-ABP Treatment on Virus Growth

| Virus | Virus Titer | | % Inhibition |
|---|---|---|---|
| | +6-ABP | −6-ABP | |
| CMV | $1 \times 10^3$ | $1 \times 10^4$ | 90 |
| RSV | $1 \times 10^5$ | $1 \times 10^5$ | 0 |
| Influenza | $1 \times 10^4$ | $1 \times 10^4$ | 0 |
| Adenovirus | $1 \times 10^2$ | $1 \times 10^2$ | 0 |
| HSV-2 | $2 \times 10^5$ | $1.6 \times 10^6$ | 87.5 |
| Enterovirus | $1.6 \times 10^6$ | $1.6 \times 10^6$ | 0 |

EXAMPLE 3

6-ABP Inhibitory Effect on the Activation of HIV by Specific DNAs

This example illustrates the inhibitory effect of 6-ABP on the activation of HIV by specific DNAs.

In one series of experiments, the effect of HSV IE110 and CMV IE2 gene expression on HIV replication using the syncytium assay formation on MT2 cells that defines HIV growth was examined. The ability of 6-ABP to inhibit HIV growth activation was studied in duplicate cultures. U937 cells were transfected with HSV IE110 CMV IE genes or mock transfected with pBR322 plasmid and duplicate cells were pretreated with HIV. Virus (HIV) growth was assayed at various times thereafter. HIV titers are expressed as syncytia forming units/ml.

Transfection was 24 hours before HIV infection. Sampling was done at days 3, 5, 6, and 8 post infection with HIV. 6-ABP treatment was 24 hours prior to transfection in order to allow intercellular 6-ABP concentration to equilibrate with external drug concentration. The timing chosen and drug dosage relate to drug penetration. The SFU assay consists of the method of Harada described in *Science*, 299:563, (1985) modified according to *Virology*, 167:299 (1988) for direct microscopic quantitation of syncytia.

The results, shown in Table 2, indicate that HIV replication is enhanced 100 fold by transfection of U937 cells with HSV IE110 at days 6 and 8 (Group 4). Separate experiments showed that it is also activated 7 fold by exposure to CMV IE. Exposure to 1 mM 6-ABP virtually abrogates activation by HSV IE110 presumably by virtue of its inhibitory effect on HSV IE110 gene expression. These findings are virtually identical to those obtained in the CAT assay.

TABLE 2

HIV GROWTH IN 6-ABP TREATED CELLS

| | U937 | SFU/ml | | | |
|---|---|---|---|---|---|
| GROUP | Day | 3 | 5 | 6 | 8 |
| 1 | U937 Untreated | 27 | 107 | 107 | 133 |
| 2 | U937 + 6-ABP | 13 | 10 | 10 | 10 |
| 3 | U937 + PBR Mock Transfection | 32 | 250 | 250 | 250 |
| 4 | U937 + HSV IE110 | 160 | 350 | 15,000 | 15,000 |
| 5 | U937 + HSV IE110 + 6-ABP (1 mM) | 32 | 64 | 100 | 100 |

HIV titers are expressed as syncytia forming units/ml.

6-ABP caused a significant reduction in HIV growth even in the absence of the activating HSV gene. This is consistent with the findings that 6-ABP has a great inhibitory effect on HIV growth.

EXAMPLE 4

This example illustrates the effect of 6-ABP on HSV and CMV mediated HIV activation in macrophages.

To determine the effect of 6-ABP on HSV and/or CMV mediated HIV activation in macrophages, U937 cells were co-transfected with HIV-LTRcat, the known transactivator genes of HSV and CMV, and assayed for CAT expression using methods described in Methods and Materials. The results are summarized in Table 3.

TABLE 3

Effect of 6-ABP on HIV-LTR Activation

| Exp | DNA Added | Fold Activation |
|---|---|---|
| 1. | pBR322 (Control) | 0 |
| 2. | HSV-IE-110 | 125 |
| 3. | HSV-IE-175 | 1 |
| 4. | HSV-IE-110 + 6-ABP (5 mM) | 20 |
| 5. | PBR322 + 6-ABP | 0 |

As shown in Table 3, co-transfection of U937 cells with HIV-LTRcat and HSV-IE110 or CMV IE2 genes resulted in a significant 125 fold activation of HIV-CAT expression experiment 2. This activation was greatly reduced to 0–10 fold as seen when experiments 2 and 4 are compared. Introduction of HSV IE175 did not enhance HIV-CAT expression in these cells as seen from experiment No. 3.

EXAMPLE 5

Direct Anti-HIV Effects of 6-ABP in Established Cell Lives in Culture

This example illustrates a direct inhibitory effect of 6-ABP on HIV replication in established cell cultures.

The effects of 6-ABP treatment of AA-2 cells was directly analyzed by cell count and viability tests including cloning efficiency and trypan blue uptake. The AA2 cell culture having initial cell count per well $0.5 \times 10^5$ was submitted to treatment with 3 mM of 6-ABP and compared to untreated (Control) cell culture. The cells were counted 4 days after the treatment with 6-ABP. Results are illustrated in Table 4.

TABLE 4

|  | Initial Cell Count/Well | Cell Count After 4 days |
| --- | --- | --- |
| Control | $0.5 \times 10^5$ (± 20%) | $1.5 \times 10^5$ (± 30%) |
| 6-ABP (3 mM) | $0.5 \times 10^5$ (± 20%) | $0.7 \times 10^5$ (± 35%) |

Viability test gave no evidence of toxic effects of 6-ABP.

It is evident that both 6-ABP exerts an inhibitory effect on cell proliferation, coincidental with the complete abrogation of HIV replication. However, the slowing down of cell replication in AA-2 cells does not coincide with any detectable cellular toxicity, a phenomenon that predicts a cytostatic anticancer effect of other drugs. This is unique, inasmuch it does not involve cytotoxicity.

EXAMPLE 6

HSV Binding at the Site of Replication

This example illustrates HSV DNA binding at the site of replication ($ori_s$) initiation at ADPRT.

The 230 bp XbaI-HindIII $ori_s$ DNA of HSV-1 was isolated from plasmid pKC4 and radioactively labeled with [32P] dCTP by fill-in reaction with the Klenow form of *E. coli* DNA polymerase. Labeled DNA fragments were purified as previously described in *J. Virol.*, 63:2773 (1989).

A nitrocellulose filter binding assay based on the method described in *J. Biol. Chem.*, 263:1505 (1988) was used to determine the specific binding of ADPRT to $ori_s$ DNA. Nitrocellulose filters (Schleicher and Schuell, BA 85, 0.47 um pore size, 27 mm diameter) were presoaked for 60 minutes in binding buffer (250 mM Tris-Cl, pH 8.0, 100 mM MgCl2, 1000 mM NaCl, 0.6 mM DTT, 0.1 mg/ml BSA, 0.1 mM PMSF and 0.1 mM TLCK). 5 ul of [32P] $ori_s$ DNA was added to 210 ul of cold binding buffer and incubated for 1 minute. 2 ul of either ADPRT (200 ng) or HSV-1 infected Vero cell extract (Vero(F), 2 ug) was then added to the DNA solution and incubated for 10 minutes at 25° C. Samples were transferred to ice, followed by filtration through the nitrocellulose filters. The filters were then washed four times with cold wash buffer containing 25 mM Tris-Cl, pH 8.0, 10 mM MgCl2, 0.5 mM DTT, 100 mM NaCl, 5% DMSO. The filters were dried and the amount of radioactive material bound to the filters was determined by scintillation spectrophotometry.

Results are expressed as the average of duplicate samples, with input $ori_s$ DNA was 8,000/sample and are shown in Table 5.

TABLE 5

| Sample | CPM Bound to Filter | % Specific Bound |
| --- | --- | --- |
| $Ori_s$ DNA alone | 172 |  |
| $Ori_s$ DNA + Vero (F) | 1220 | 13.2 |
| $Ori_s$ DNA + ADPRT | 6384 | 78.6 |

The results suggest that the binding of ADPRT to the $ori_s$ DNA fragment of HSV-1 is specific and is significantly stronger than that observed previously in *Proc. Natol. Acad. Sci.*, 85:2959 (1988) for an infected cell extract containing HSV-1 origin binding proteins. Under the conditions examined, DNA binding to filter alone was minimal while ADPRT complexed to $ori_s$ DNA in a manner sufficient to bind nearly 80% of available DNA.

EXAMPLE 7

Inhibition of HIV Proliferation in Human Lymphoblasts Obtained from AIDS Patients This example illustrates inhibitory effect of 6-ABP on HIV proliferation in human lymphoblasts obtained from AIDS patients.

The HIV isolates used in these experiments were isolated from the blood of infected patients. After isolation, HIV infection was established in CEM cells, and these infected cells were used to produce a stock of HIV virus that was titered to measure the concentration of tissue culture infective doses (TCID).

6 ABP was dissolved in saline in amount which was further diluted as required, and added to the culture medium containing cells at the indicated concentrations.

Human peripheral blood mononuclear cells from a non-infected, normal individual were stimulated for 2 to 3 days with phytohemagglutinin in tissue culture, washed, aliquoted and cultured overnight with 200 TCID or 50 TCID of HIV and were untreated or treated with 0.01, 0.1, 1.0 or 10.0 mM 6-ABP. An additional control was incubated with 10 mM 6-ABP without presence of HIV. After the overnight incubation, residual. The cells were placed in culture in medium containing IL-2, but in the absence of additional 6-ABP, and monitored at 6 days and 12 days for the production of HIV-p24 core antigen, or for measurements of particulate reverse transcriptase. A decrease in the amount of either of these indicators of HIV indicated an inhibition by 6-ABP in the ability of HIV to replicate in normal human lymphoblasts.

HIV p24 antigen was measured by ELISA, with a cutoff of 5 pgm/ml. Particulate reverse transcriptase was measured by centrifuging down free virus from tissue culture fluids, lysing HIV in a buffer containing detergent, magnesium, H3-labelled dTTP and poly rA.oligo dT primer, incubating for 1 hour, and measuring precipitable radioactivity, expressed as cpm per volume of HIV-containing medium.

The viability of lymphoblasts was measured by incubating the cells exposed to IL-2, HIV and to 6-ABP with H3-thymidine for 6 hours on the sixth day of culture and determining the amount of cpm incorporated per 100,000 cells placed in culture.

The results are shown in FIG. 10 which displays a typical experiment with surviving human lymphoblasts which were exposed to the drug only for 18 hours. A dramatic decrease of HIV (p24 tests) occurred already at 0.1 mM 6-ABP concentration at 6 (lower curve) or 12 days past infection (upper curve). Abscissa shown the concentration of 6-ABP.

In order to ascertain that relatively short 18 hours exposure of human lymphoblasts selectively blocks HIV replication and has minimal effects on DNA synthesis of lymphoblasts, the proliferation, p24 and reverse transcriptase experiments were also performed, as shown in FIG. 11.

In panel A (top) DNA synthesis of lymphoblasts is assayed as a function of 6-ABP concentration. In panel A' (lower curve) the decay of HIV replication is simultaneously determined, and in A "panel" reverse transcriptase was assayed. All these are accepted assays for HIV replication.

From FIG. 11 it is evident that during 18 hr. exposure to the 6-ABP, there is a great selectivity of 6-ABP against HIV replication, leaving cellular DNA synthesis virtually unaffected.

Exposing lymphoblasts for 4 consecutive days in varying concentrations of 6-ABP, panels B and B' had also an inhibitory effect on lymphoblast DNA synthesis measured by thymidine incorporation. However the viability of lymphoblasts was not affected by the drug, since no cell death occurred and thus the inhibition is temporary and reversible. Thus the antiproliterative effect of 6-ABP can be accomplished without detectable cell damage or death, in contrast to any of the currently employed or available cytostatic. It follows that appropriate i.v. infusion treatment of AIDS patients by 6-ABP can be performed without serious toxic effects on lymphoblasts.

EXAMPLE 8

6-ABP Toxicity Studies

This example illustrates the lack of toxicity after intraperitoneal administration of 6-ABP to mice.

Two toxicological tests administering 6-ABP to mice were performed under the following conditions.

Study 1:

One group of 5 mice received 6-ABP i.p. injection in amount of 1 g/kg. Mice were observed for 24 hours. There were no toxic symptoms in 4 mice in the group. One mouse developed, 4 hours after the injection, seizures and hind leg weakness but then completely recovered in 18 hours.

Study 2:

Group of 50 white mice was injected daily with 250 mg/kg 6-ABP i.p. for 12 days. There were no visible toxic effects. Mice behavior was quite normal, there was no disruption in their normal weight gain.

We claim:

1. A method of inhibiting viral growth and replication within a cell in the substantial absence of cellular toxicity comprising contacting a cell selected from the group consisting of human immunodeficiency virus, herpes simplex virus type 1, herpes simplex virus type 2 and cytomegalovirus with an effective amount of a compound or salt thereof, having the formula:

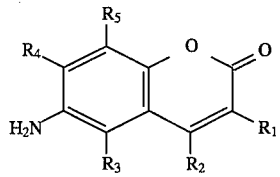

in combination with an effective amount of an inert carrier wherein $R_1$, $R_2$, $R_3$, $R_4$, or $R_5$ are, independent from one another, selected from the group consisting of hydrogen, hydroxy, amino, ($C_1$–$C_6$) alkyl, ($C_1$–$C_5$) alkoxy, ($C_3$–$C_8$) cycloalkyl, phenyl, phenyl substituted with alkyl, alkoxy, hydroxy, or halogen.

2. The compound of claim 1 wherein $R_1$, $R_2$, $R_3$, $R_4$ or $R_5$ are hydrogen.

3. The method of claim 1, wherein the virus is human immunodeficiency virus.

4. The method of claim 1, wherein the virus is herpes simplex virus type 1 or type 2.

5. The method of claim 1, wherein the virus is cytomegalovirus.

6. The method of claim 1, wherein the cell is in a subject in need of an anti-viral treatment.

7. The method of claim 1 wherein the composition is administered by intravenous injection.

8. The method of claim 6 wherein the composition is administered in amount of 0.1 to 100 mg/kg/day.

9. A method of inhibiting viral growth and replication within a cell in the substantial absence of cellular toxicity comprising contacting a cell selected from the group consisting of human immunodeficiency virus, herpes simplex virus type 1, herpes simplex virus type 2 and cytomegalovirus with effective amount of a compound having the formula:

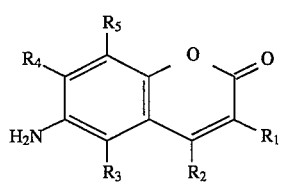

wherein $R_1$, $R_2$, $R_3$, $R_4$, or $R_5$ are, independent from one another, selected from the group consisting of hydrogen, hydroxy, amino, ($C_1$–$C_6$) alkyl, ($C_1$–$C_5$) alkoxy, ($C_3$–$C_8$) cycloalkyl, phenyl, phenyl substituted with alkyl, alkoxy, hydroxy, or halogen.

* * * * *